US011584526B2

(12) United States Patent
Lepek et al.

(10) Patent No.: US 11,584,526 B2
(45) Date of Patent: Feb. 21, 2023

(54) CONTINUAL AERAIL, RELEASE FROM DRONES

(71) Applicant: Senecio Ltd., Kfar-Saba (IL)

(72) Inventors: Hanan Lepek, Kfar-Saba (IL); Rom Eisenberg, Kfar-Saba (IL); Yoram Fleischmann, Kibbutz Lehavot Haviva (IL); Amir Ilan, Rehovot (IL)

(73) Assignee: Senecio Ltd., Kfar-Saba (IL)

( * ) Notice: Subject to any disclaimer, the term of this patent is extended or adjusted under 35 U.S.C. 154(b) by 357 days.

(21) Appl. No.: 16/082,546

(22) PCT Filed: Mar. 9, 2017

(86) PCT No.: PCT/IL2017/050304
§ 371 (c)(1),
(2) Date: Sep. 6, 2018

(87) PCT Pub. No.: WO2017/154004
PCT Pub. Date: Sep. 14, 2017

(65) Prior Publication Data
US 2019/0092471 A1 Mar. 28, 2019

Related U.S. Application Data

(60) Provisional application No. 62/307,471, filed on Mar. 12, 2016, provisional application No. 62/306,732, filed on Mar. 11, 2016.

(51) Int. Cl.
*B64D 1/12* (2006.01)
*A01K 67/033* (2006.01)
(Continued)

(52) U.S. Cl.
CPC .............. *B64D 1/12* (2013.01); *A01K 67/033* (2013.01); *B64C 39/024* (2013.01); *B64D 1/00* (2013.01);
(Continued)

(58) Field of Classification Search
CPC .... B64D 1/00; B64D 1/02; B64D 1/12; B64C 39/024
See application file for complete search history.

(56) References Cited

U.S. PATENT DOCUMENTS 4,260,108 A * 4/1981 Maedgen, Jr. ......... A01N 63/00
222/161
5,148,989 A * 9/1992 Skinner .................... B64D 1/18
239/128
(Continued)

FOREIGN PATENT DOCUMENTS

| AU | 2015100998 | 12/2015 |
| CN | 105035325 | 11/2015 |

(Continued)

OTHER PUBLICATIONS

Written Opinion dated Dec. 20, 2019 From the Intellectual Property Office of Singapore, IPOS Re. Application No. 11201810004S. (7 Pages).

(Continued)

*Primary Examiner* — Michael H Wang

(57) ABSTRACT

A storage and release mechanism for aerial distribution and release of insects from an unmanned aerial vehicle, the release being aimed at controlling a wild insect population, the wild population having fluctuating local densities, the mechanism comprising a switch for switching between two or more different sustainable insect delivery rates for release of the insects. The method is particularly suitable for sterile male mosquitoes in programs to control wild mosquito populations.

20 Claims, 28 Drawing Sheets

(51) Int. Cl.
　　　*B64C 39/02*　　　(2023.01)
　　　*B64D 1/00*　　　(2006.01)
(52) U.S. Cl.
　　　CPC .. *B64C 2201/021* (2013.01); *B64C 2201/027* (2013.01); *B64C 2201/128* (2013.01)

(56) References Cited

U.S. PATENT DOCUMENTS

| | | | | |
|---|---|---|---|---|
| 5,718,377 | A * | 2/1998 | Tedders | A01N 63/10 239/8 |
| 6,003,782 | A * | 12/1999 | Kim | B64D 47/08 169/53 |
| 7,717,356 | B2 * | 5/2010 | Petersen | B64D 1/18 239/8 |
| 8,967,029 | B1 * | 3/2015 | Calvert | B64D 1/02 89/1.11 |
| 9,346,546 | B2 * | 5/2016 | Markov | B64D 1/16 |
| 9,505,496 | B2 * | 11/2016 | Markov | B64D 1/08 |
| 10,568,309 | B2 * | 2/2020 | Massaro | A01K 29/005 |
| 11,027,294 | B2 * | 6/2021 | Roy | B05B 12/087 |
| 2003/0192992 | A1 * | 10/2003 | Olsen | B64D 9/00 244/137.1 |
| 2005/0072880 | A1 * | 4/2005 | Nolan | B64D 1/16 244/136 |
| 2005/0127242 | A1 * | 6/2005 | Rivers | B64D 1/02 244/137.1 |
| 2014/0246545 | A1 * | 9/2014 | Markov | B64C 39/024 244/190 |
| 2015/0041593 | A1 * | 2/2015 | Markov | B64D 1/08 244/137.1 |
| 2015/0041596 | A1 * | 2/2015 | Markov | B64C 39/024 244/190 |

FOREIGN PATENT DOCUMENTS

| | | |
|---|---|---|
| WO | WO 2016/088127 | 6/2016 |
| WO | WO 2016/088128 | 6/2016 |
| WO | WO 2016/088129 | 6/2016 |
| WO | WO 2017/154004 | 9/2017 |

OTHER PUBLICATIONS

International Preliminary Report on Patentability dated Jun. 12, 2018 From the International Preliminary Examining Authority Re. Application No. PCT/IL2017/050304. (17 Pages).

International Search Report and the Written Opinion dated May 29, 2017 From the International Searching Authority Re. Application No. PCT/IL2017/050304. (14 Pages).

Written Opinion dated Mar. 13, 2018 From the International Preliminary Examining Authority Re. Application No. PCT/IL2017/050304. (6 Pages).

Patent Examination Report dated Apr. 20, 2021 From the Australian Government, IP Australia Re. Application No. 2017231049. (6 Pages).

Notification of Office Action and Search Report dated Aug. 4, 2021 From the State Intellectual Property Office of the People's Republic of China Re. Application No. 201780016421.5 and Its Translation of Office Action Into English. (40 Pages).

Notification of Office Action dDated May 6, 2022 From the National Intellectual Property Administration of the People's Republic of China Re. Application No. 201780016421.5 and Its Translation Into English. (30 Pages).

Search Report and Written Opinion dated Jan. 17, 2020 From the Intellectual Property Office of Singapore, IPOS Re. Application No. 11201810004S. (17 Pages).

Tarim Khurana "Continual Aerial Release From Drones", IP, Abstract, Sep. 29, 2018.

* cited by examiner

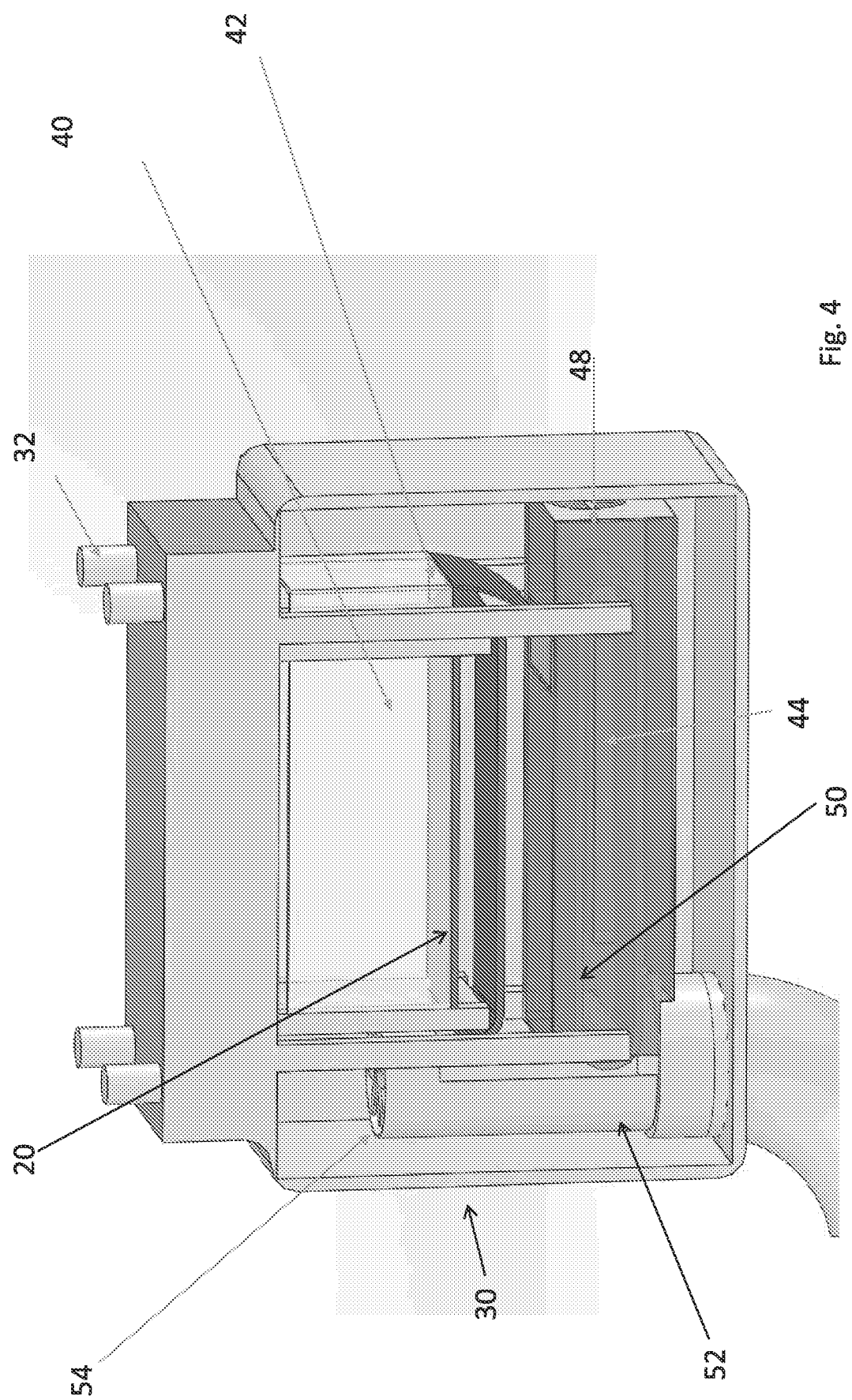

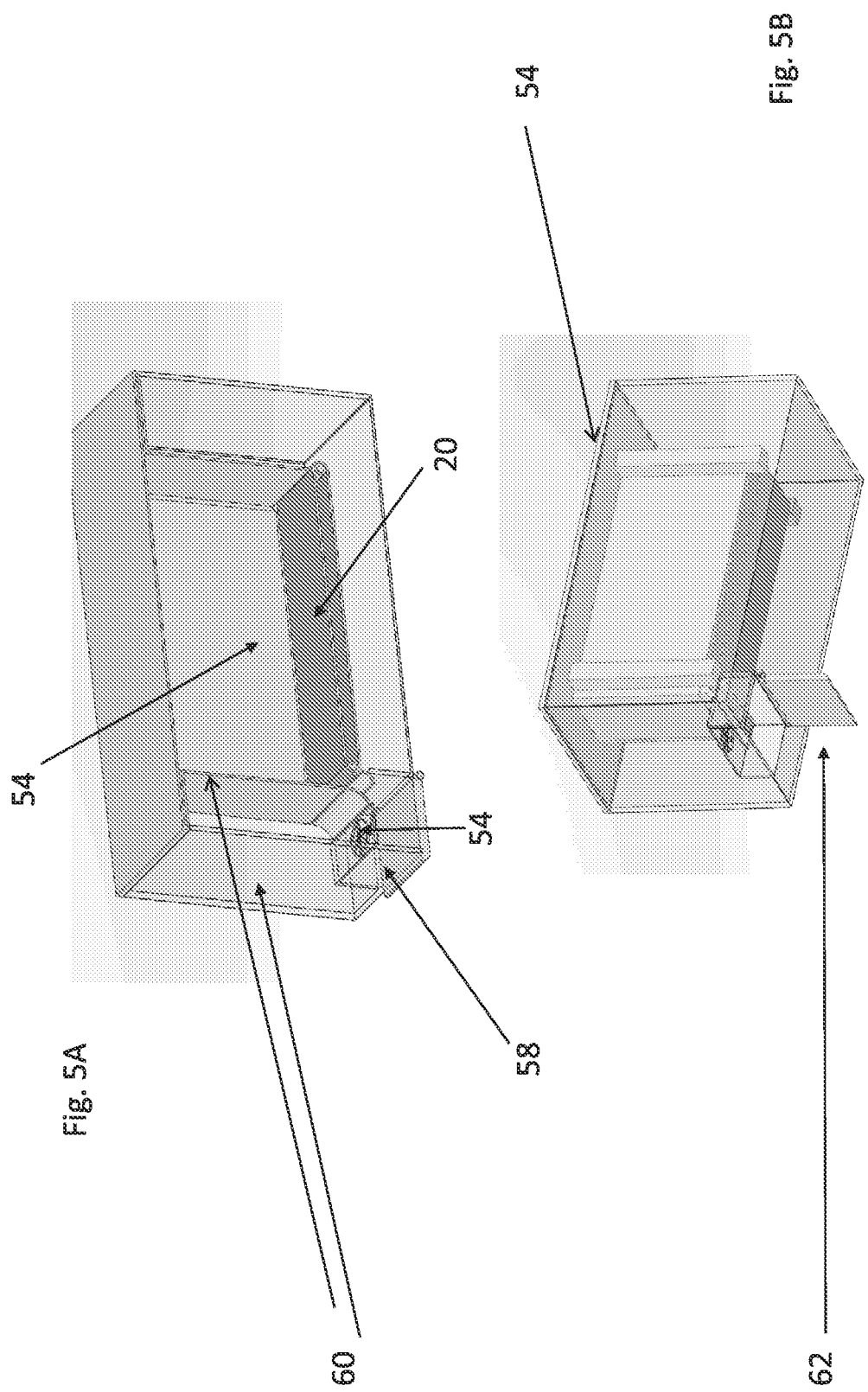

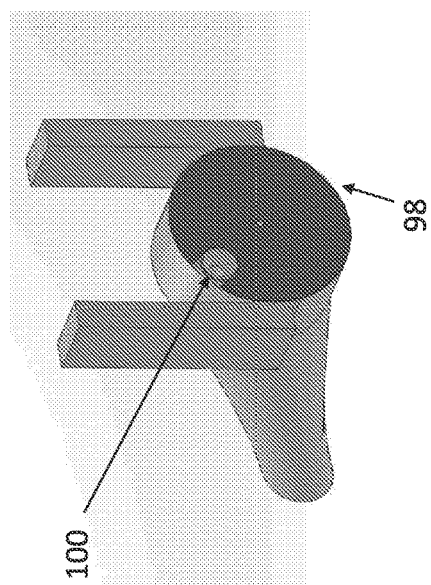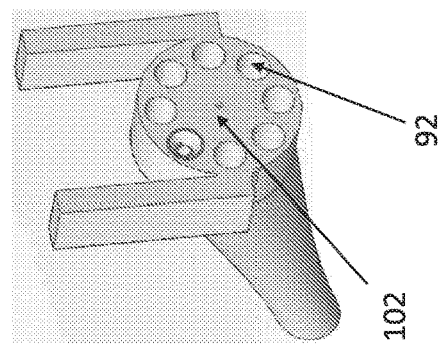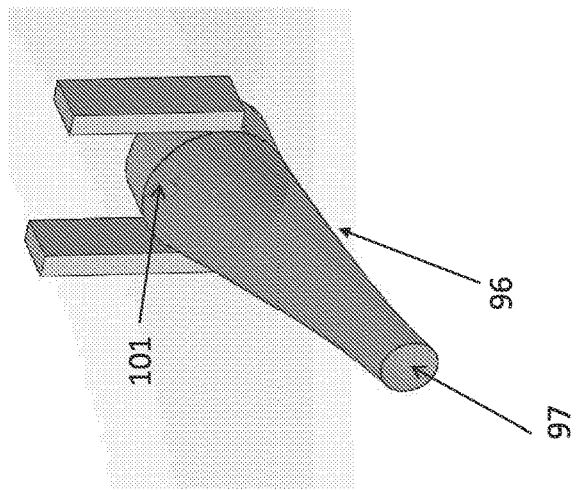
Fig. 9

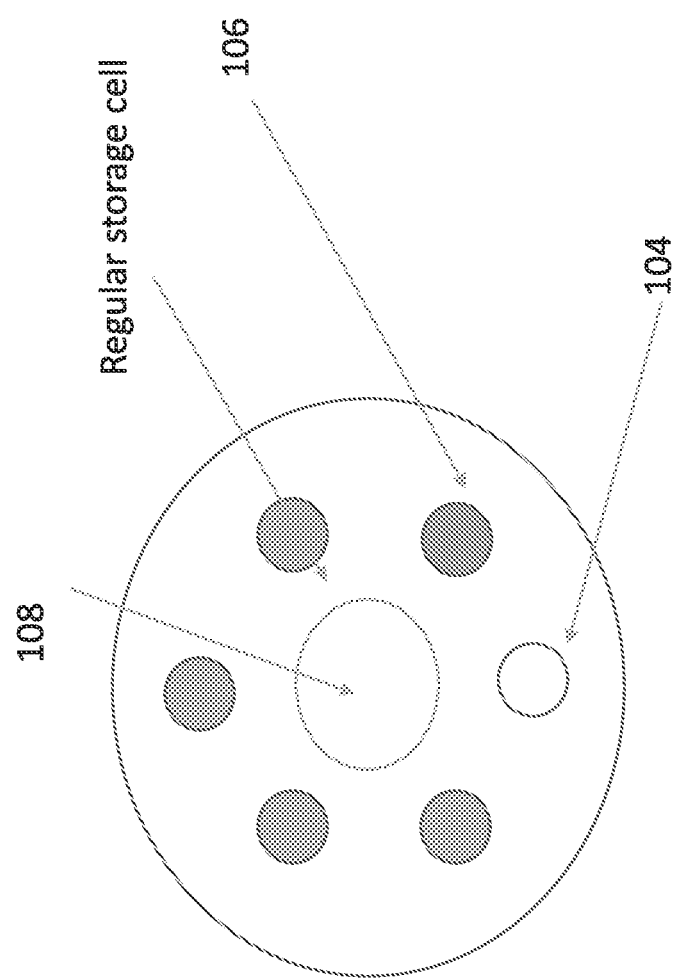
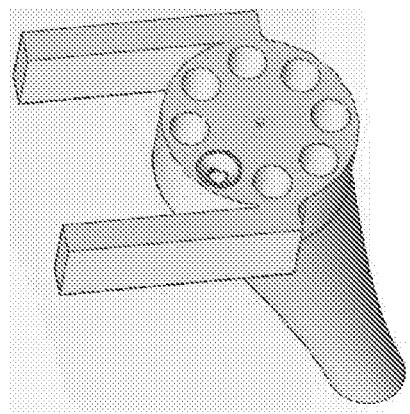
Fig. 10

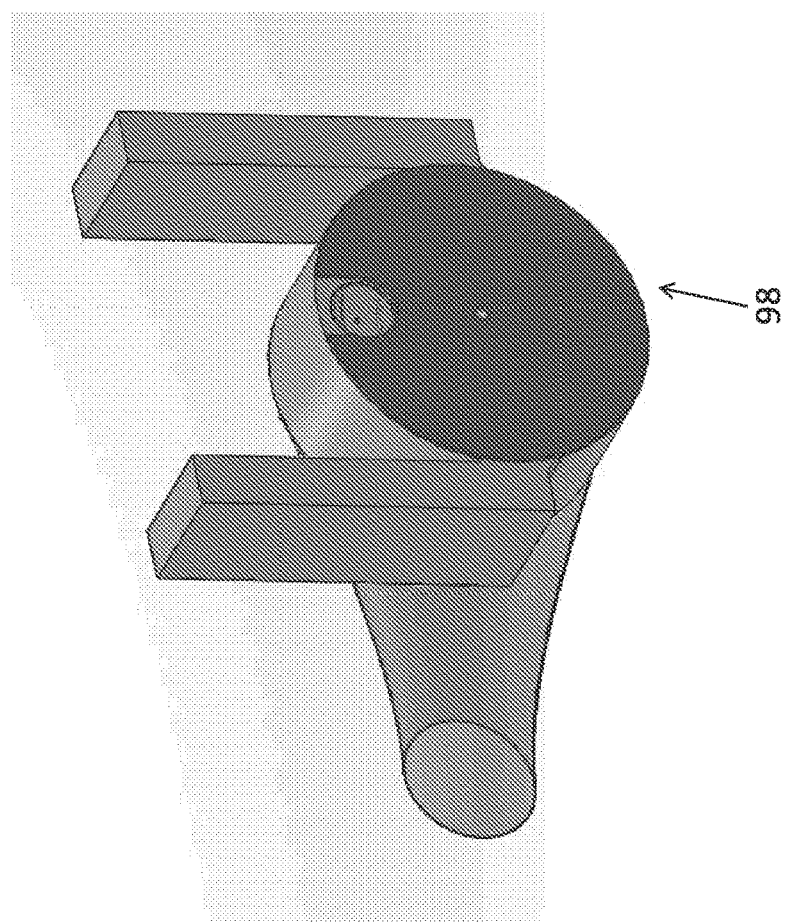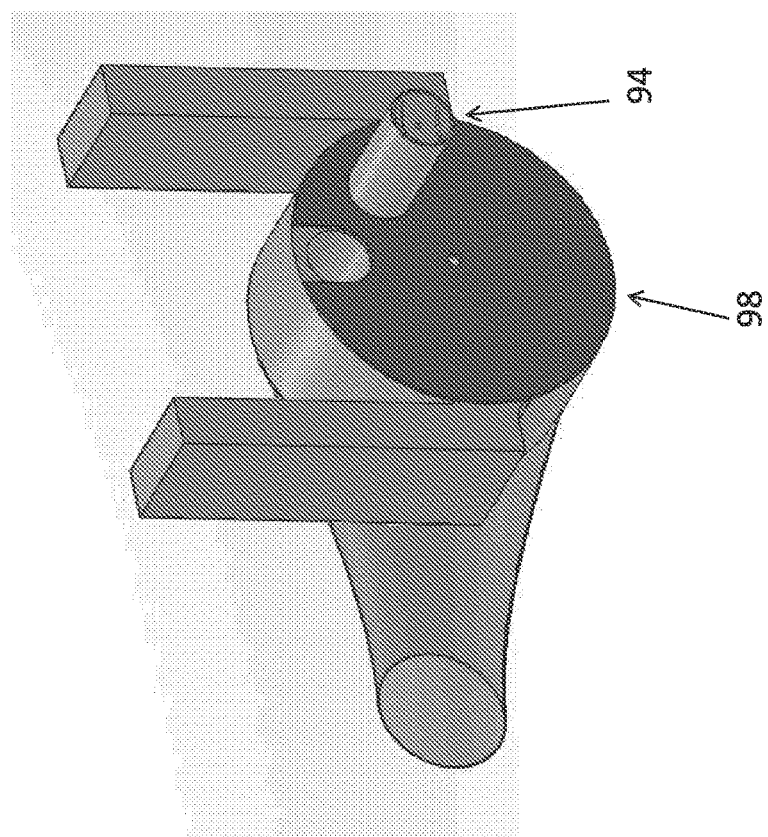
Fig. 11

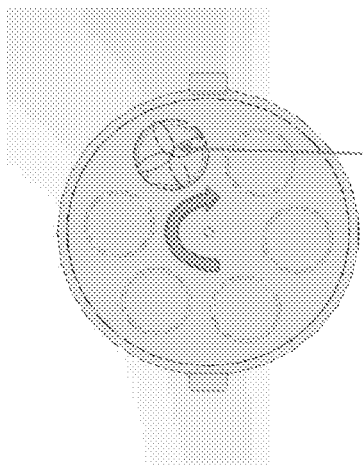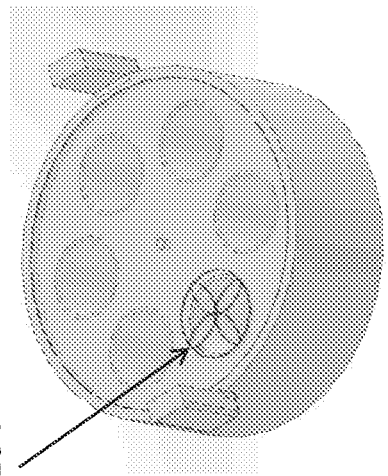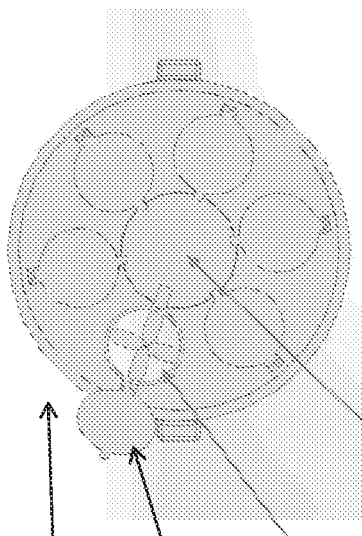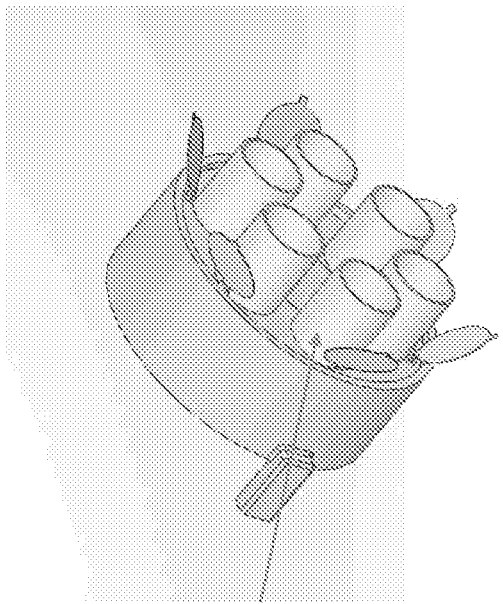

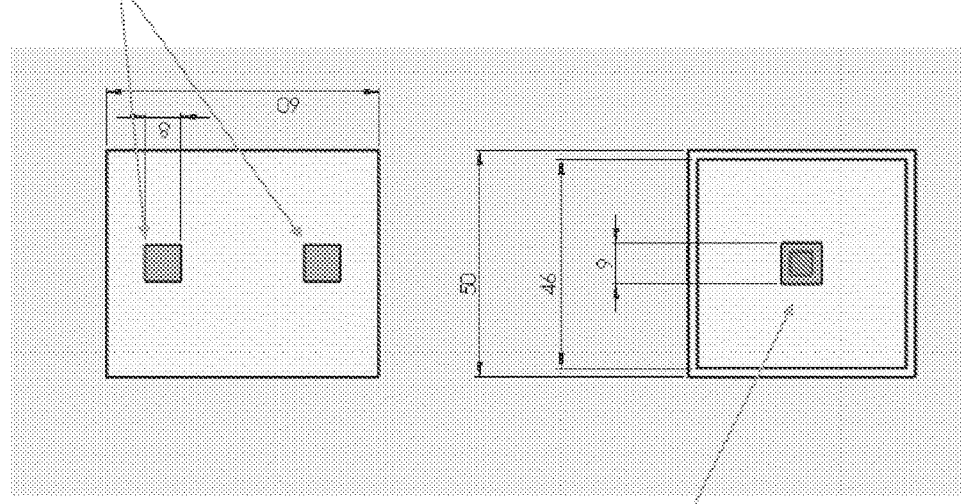

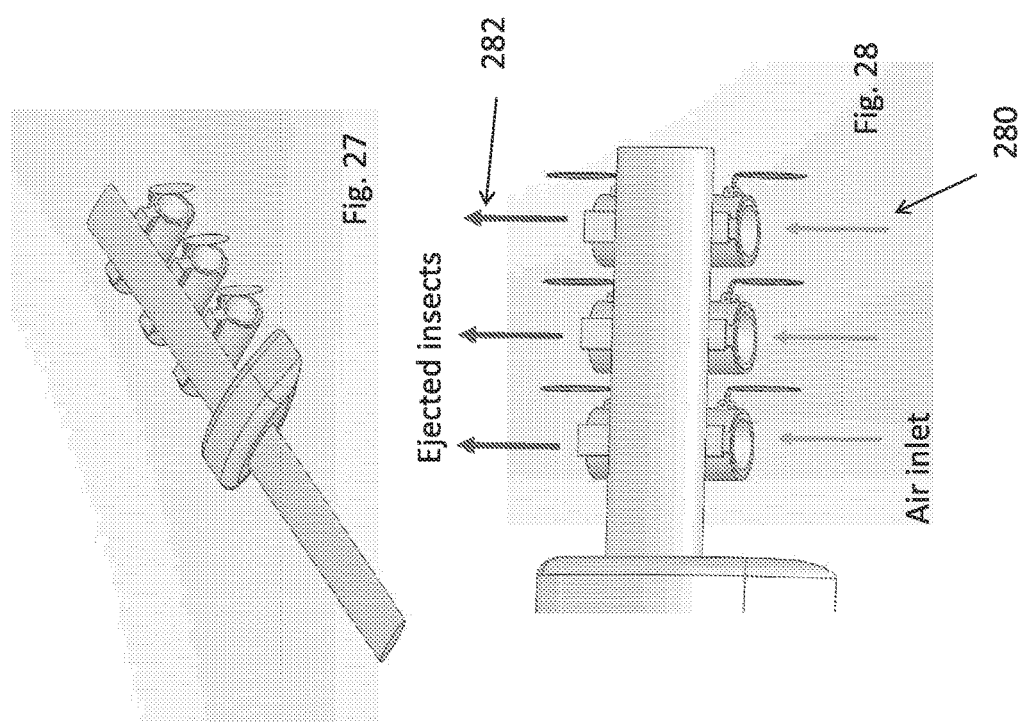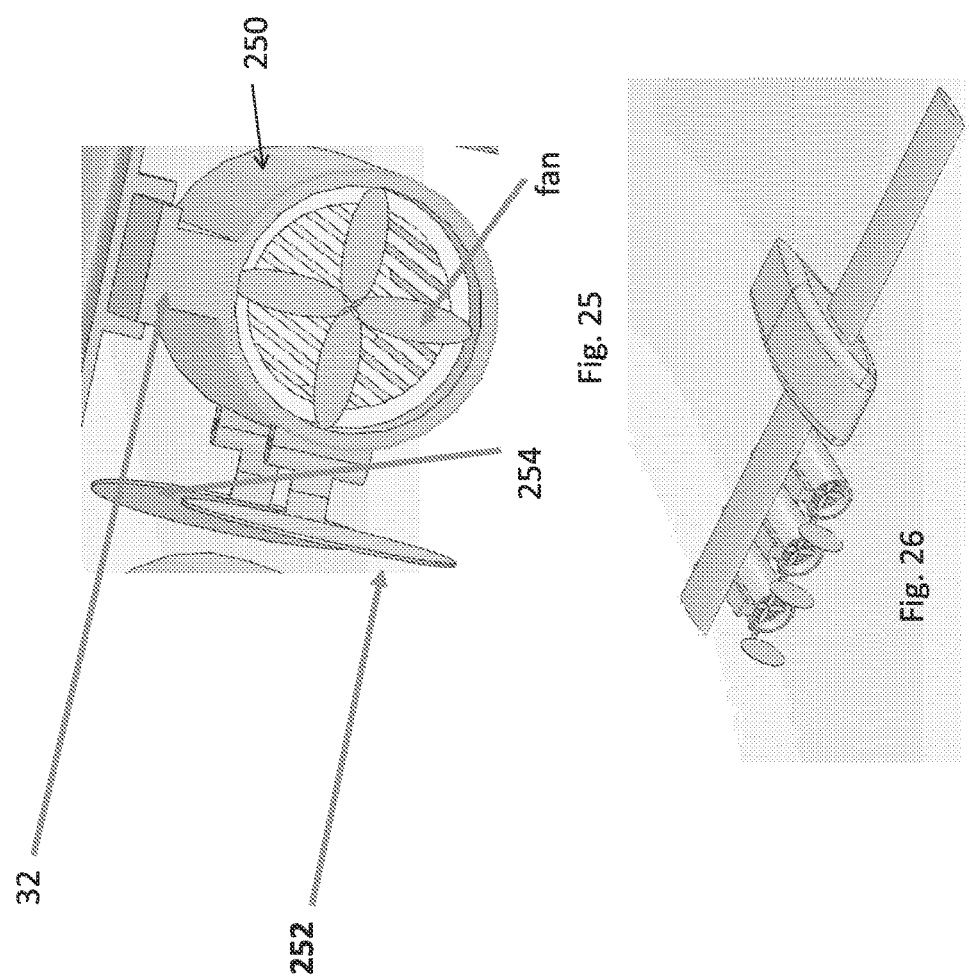

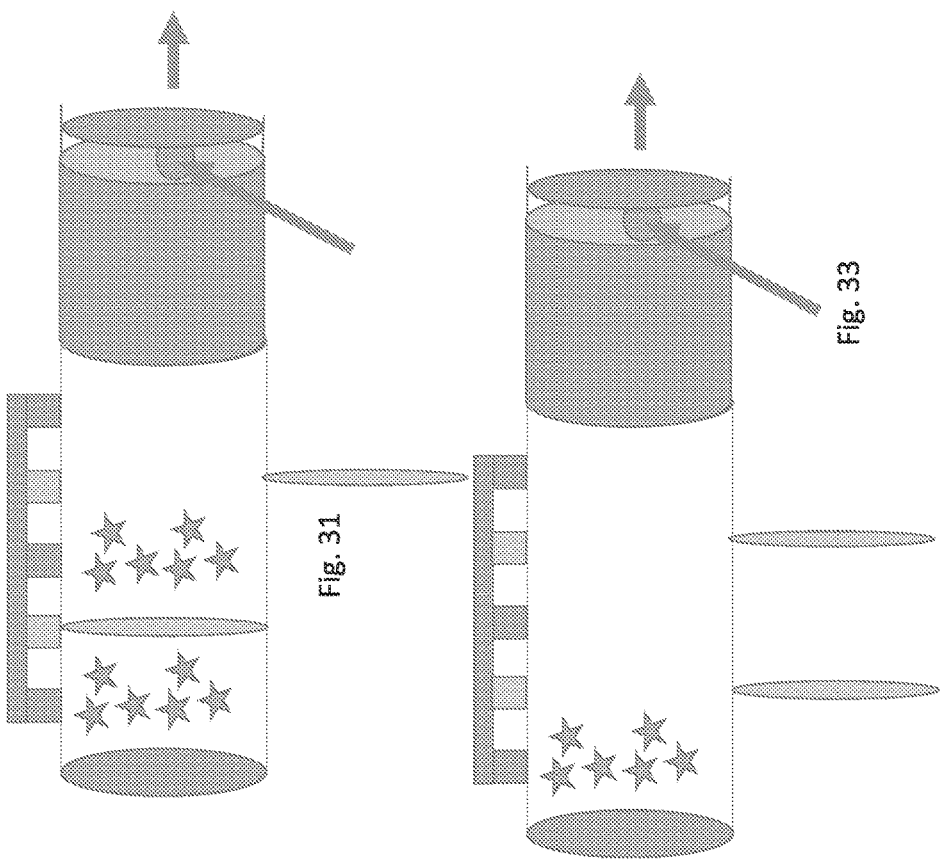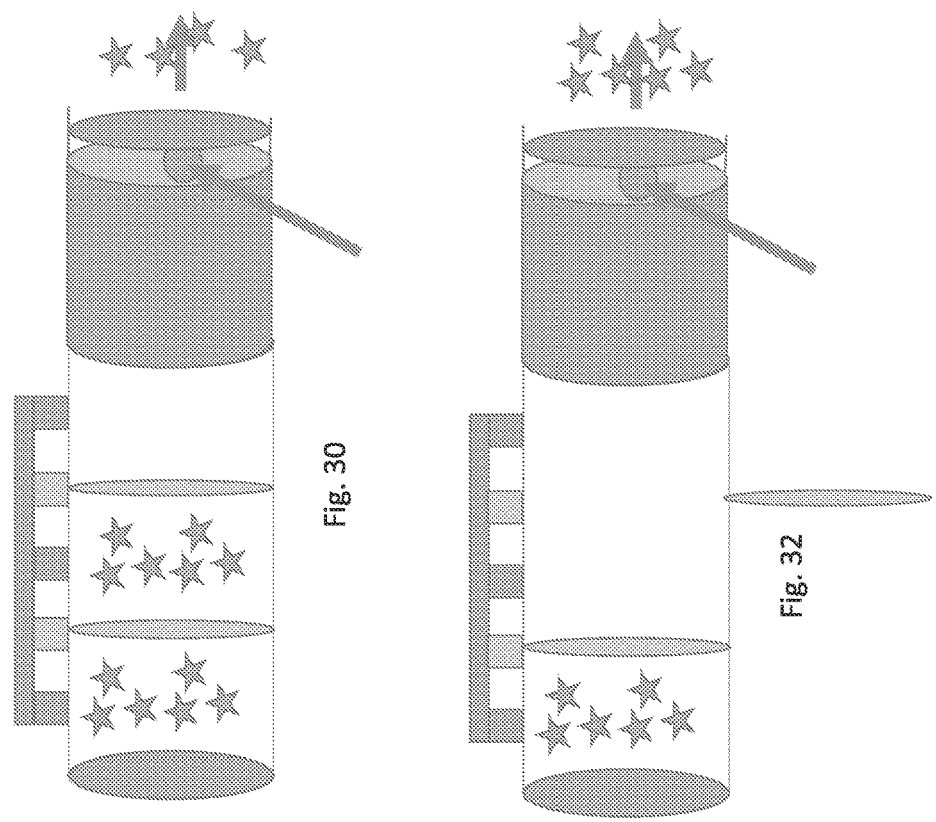

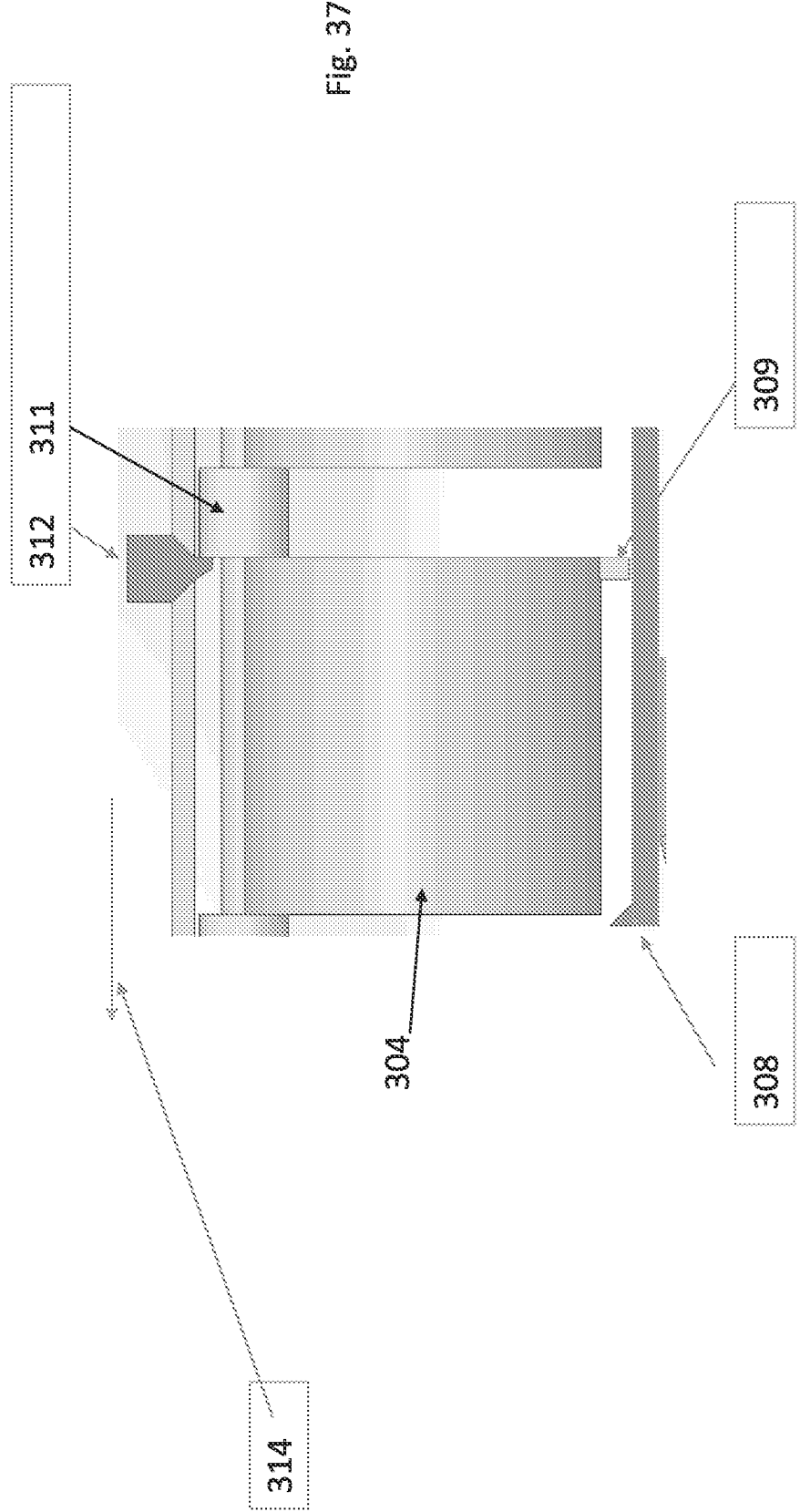

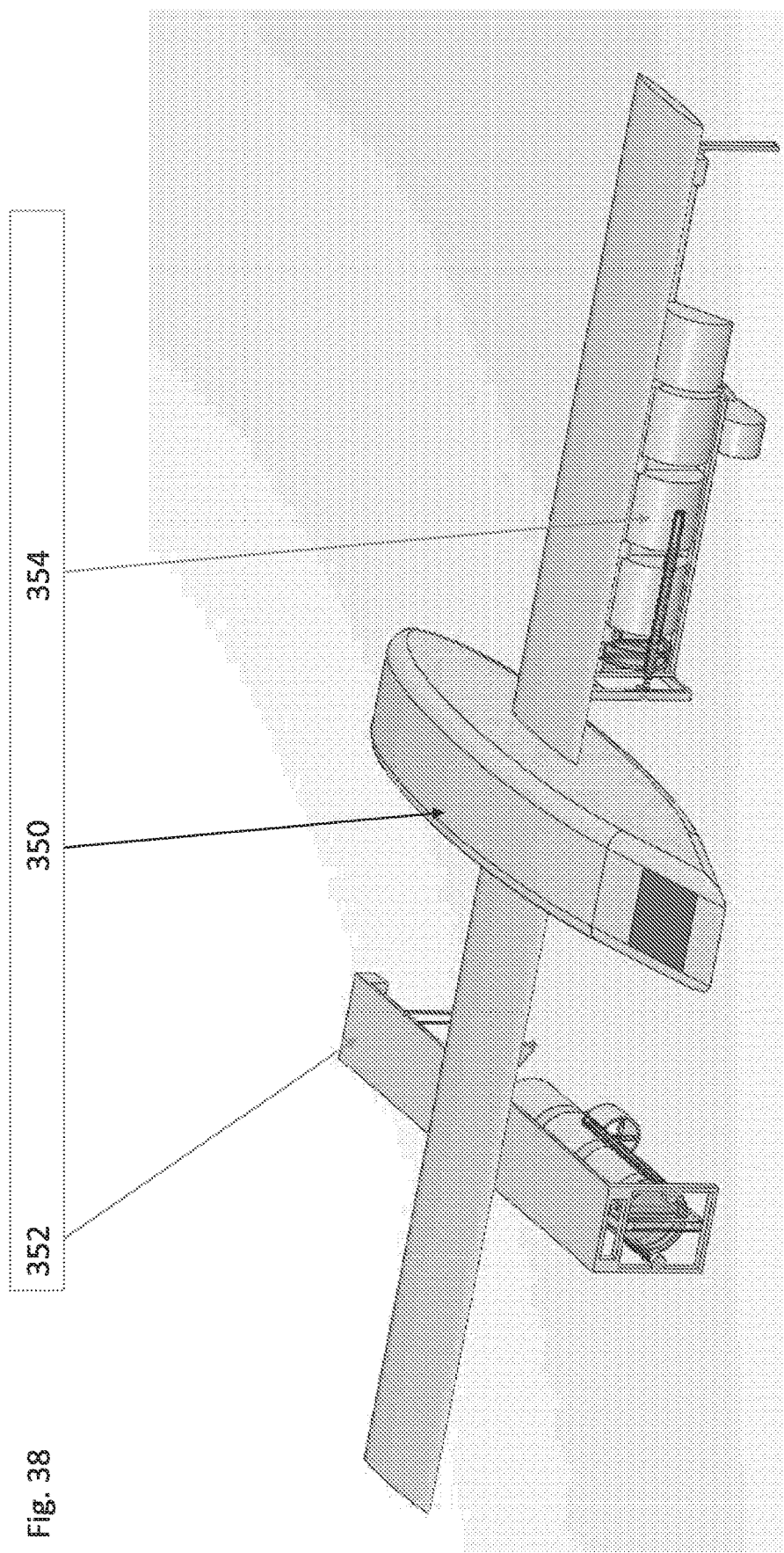

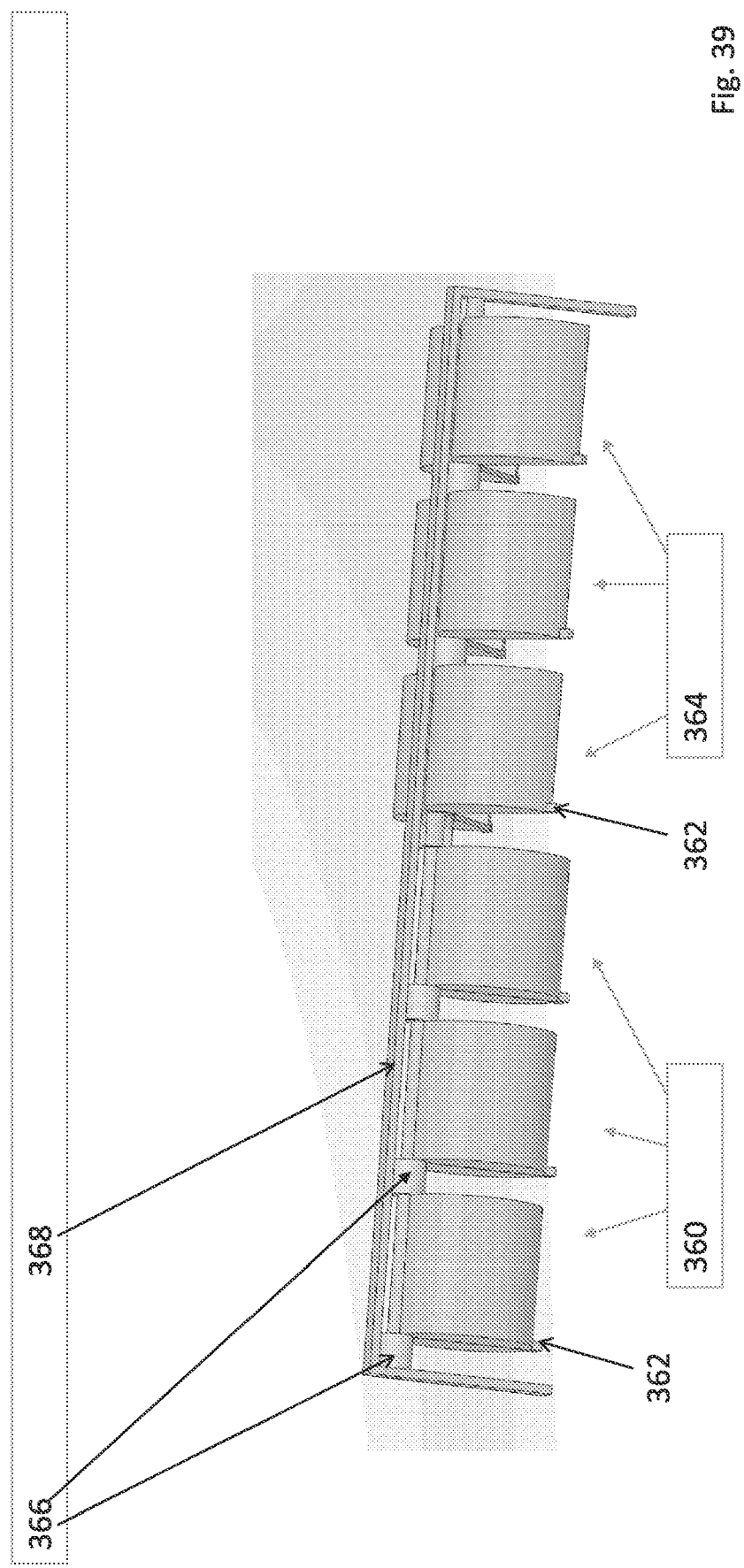

Different views of the set of cells

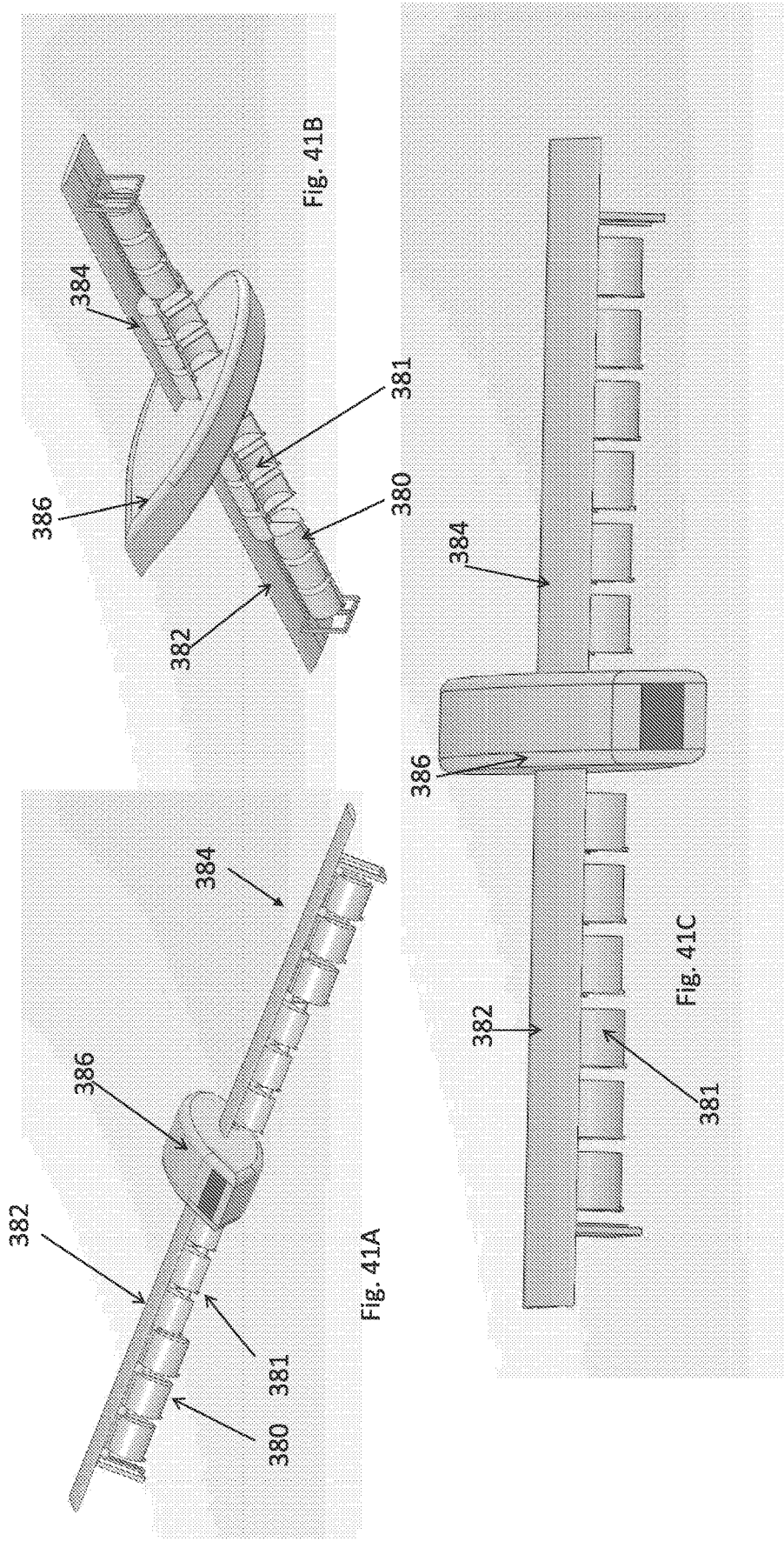

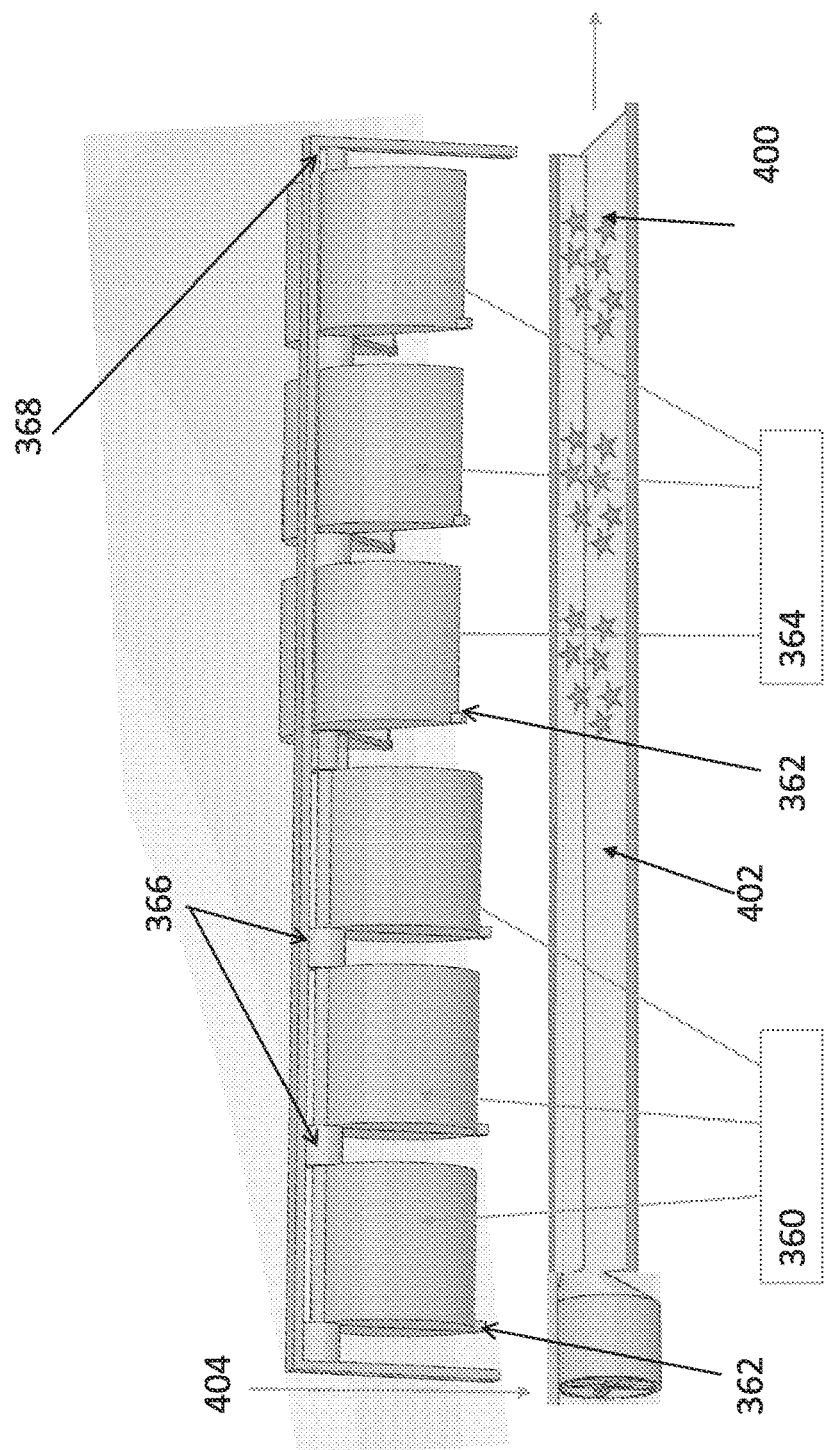

CONTINUAL AERAIL, RELEASE FROM DRONES

RELATED APPLICATIONS

This application is a National Phase of PCT Patent Application No. PCT/IL2017/050304 having International filing date of Mar. 9, 2017, which claims the benefit of priority under 35 USC §119(e) of U.S. Provisional Patent Application Nos. 62/307,471 filed on Mar. 12, 2016 and 62/306,732 filed on Mar. 11, 2016. The contents of the above applications are all incorporated by reference as if fully set forth herein in their entirety.

FIELD AND BACKGROUND OF THE INVENTION

The present invention, in some embodiments thereof, relates to apparatus and methods for continual aerial release of insects from drones and, more particularly, but not exclusively, to a drone-borne storage and release mechanism for continual controlled and measured distribution of delicate insects such as mosquitoes, in particular delicate mosquitoes which require to be released in adult form.

Using drones to distribute insects and like invertebrates for control purposes is known. Prior art systems distribute flies and moth larvae. One known system for moth larvae placed a tube under the aircraft and when distribution was required a door was opened and a fan was started to force out the insects from the tube. A problem was experienced in that the tube emptied too fast and so the power was reduced until the tube was felt to take an optimal time to empty.

However, although they were able to find a power level that worked reasonably, they were unable to provide any more than a single dosage level. There was no flexibility in finding two different power levels that both worked and which provided different effective levels of insect distribution.

Furthermore, there are hardy insects that are fine being pushed out into the airstream, but there are also more delicate insects for whom being pushed with full force into an airstream can be fatal. Mosquitoes are relatively delicate insects.

One solution with the more delicate creatures is to distribute them as larvae, but mosquito larvae are in fact aquatic, so it is not possible to use this solution for mosquitoes.

SUMMARY OF THE INVENTION

The present embodiments provide contain and release units that can be carried by drones and can provide controlled and measured release of insects, in particular fragile insects.

The present embodiments further relate to self-opening cells that contain the insects and which can be opened one by one at a predetermined rate and location in order to achieve continual or quasi-continual or controlled distribution.

According to an aspect of some embodiments of the present invention there is provided a storage and release mechanism for aerial distribution and release of insects from an unmanned aerial vehicle, the release being aimed at controlling a wild insect population, the wild population having fluctuating local densities, the mechanism comprising a switch for switching between a first sustainable insect delivery rate for release of the insects via the unmanned aerial vehicle and a second sustainable insect delivery rate for release of the insects via the unmanned aerial vehicle.

In an embodiment, storage of the insects prior to release is in a cold storage.

In an embodiment, the insects are released from the storage onto a conveyer, the switch setting a speed of the conveyer.

In an embodiment, the insects are arranged in a sequence of radially arranged cartridges, each cartridge sequentially being brought into contact with a release mechanism.

In an embodiment, the radially arranged cartridges rotate and the release mechanism is fixed.

In an embodiment, the radially arranged cartridges are fixed and the release mechanism rotates around the cartridges.

In an embodiment, the storage is in a plurality of cartridges, each cartridge having an independently actuatable opening.

An embodiment may comprise a tube having an air inlet and an insect outlet end and a fan controllable to at least two different speeds to blow air through the tube to expel the insects.

In an embodiment, the tube has a door at the air inlet end and a door at the insect outlet end, the openings of the doors being synchronized such that the door at the insect outlet end is opened before opening of the door at the air inlet end.

In an embodiment, the fan is located at the air inlet end and pushes the insects out of the storage.

In an embodiment, the fan is located at the insect outlet end to pull the insects out of the storage.

In an embodiment, the storage is in a plurality of cartridges, each cartridge being independently openable, the mechanism further comprising a fan operated to empty a recently opened cartridge.

In an embodiment, the fan is movable towards a cartridge to be opened.

In an embodiment, the cartridge to be opened is moved towards the fan.

In an embodiment, the storage is in a plurality of cartridges, each cartridge being independently openable in a downward direction to allow gravity to cause the insects to fall out.

In an embodiment, the storage is in a plurality of cartridges and wherein the switch is configured to carry out the switching by defining a rate of opening of the cartridges.

In an embodiment, one of the sustainable insect delivery rates is set by opening at least two of the cartridges in parallel.

According to a second aspect of the present invention, there is provided a storage and release mechanism for aerial distribution and release of insects from an unmanned aerial vehicle, the release being aimed at controlling a wild insect population, the wild population having fluctuating local densities, the storage and release mechanism comprising a plurality of storage cartridges and a switch, the switch configured to switch between sequential and parallel release from the cartridges.

According to a third aspect of the present invention there is provided a storage and release method for aerial distribution and release of insects from an unmanned aerial vehicle, the release being aimed at controlling a wild insect population, the wild population having fluctuating local densities, the method comprising:

storing the insects in the unmanned aerial vehicle;

switching between a first sustainable insect delivery rate for release of the insects via the unmanned aerial vehicle and a second sustainable insect delivery rate for release of the insects via the unmanned aerial vehicle; and releasing the insects.

According to a fourth aspect of the present invention there is provided an array of self-opening containers, carried or carryable by drone, each individually controllable, to open and release insects according to desired locations and timings.

According to a fifth aspect of the present invention there is provided a storage and release mechanism for aerial distribution and release of insects from an unmanned aerial vehicle, the release being aimed at controlling a wild insect population, the mechanism comprising:

at least two cartridges containing insects for distribution, the cartridges configured for mounting on the unmanned aerial vehicle; and a controllable opening mechanism for controllably opening the cartridges to release the insects at a controllable rate.

Embodiments may comprise a magazine, wherein the at least two cartridges are contained in the magazine and wherein the magazine is mounted lengthwise along a length of a wing of the unmanned aerial vehicle.

Embodiments may comprise a magazine, wherein the at least two cartridges are contained in the magazine and wherein the magazine is mounted perpendicular to a length of a wing of the unmanned aerial vehicle.

Embodiments may comprise a magazine having a rail, wherein the at least two insect-containing cartridges comprise a plurality of insect-containing cartridges within the magazine and configured to proceed along the rail to an opening position, the opening position being associated with operation of a mechanical opener to open cells, the mechanism comprising an actuatable device to regulate arrival of cartridges at the opening position and thereby control the release rate.

Embodiments may comprise a magazine, having a collection floor, wherein the at least two insect-containing cartridges comprise a plurality of insect-containing cartridges within the magazine, the plurality of insect-containing cartridges being openable onto the collection floor; and an expulsion unit placed to disperse insects released from the cartridges towards the collection floor, wherein regulation of the expulsion unit serves to control the release rate.

Embodiments may comprise a magazine having a collection floor, wherein the at least two insect-containing cartridges comprise a plurality of insect-containing cartridges within the magazine, each cartridge having an independently actuatable opening, the plurality of insect-containing cartridges being openable onto a collection floor; and an expulsion unit placed to disperse insects released from the cartridges to the collection floor, wherein regulation of the expulsion unit serves to control the release.

According to a further aspect there is provided an unmanned aerial vehicle having at least two cartridges mounted thereon, each cartridge containing insects for release, each cartridge being controllably openable to release the insects.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 4 is a cross section of the embodiment as shown in FIG. 3;

FIGS. 5A and 5B show two views of a storage part of the embodiment of FIG. 2;

FIG. 9 shows three views of a revolving storage embodiment of the present invention;

FIG. 10 shows a variation in which the storage cells revolve; and

FIG. 11 is a detail of the embodiment of FIG. 9 showing fitting of the cartridges;

FIGS. 16-19 illustrate an alternative version of the revolving embodiment of FIG. 9;

FIGS. 21-24 illustrate an embodiment in which cartridges have independently operated shutters;

FIGS. 25-28 illustrate an embodiment in which cartridges are tubes having double doors;

FIGS. 29-33 illustrate an embodiment in which a tube cartridge divides into sub-lengths each openable separately and using suction to extract the insects;

FIG. 37 is a simplified diagram showing one of the cells of FIG. 34;

FIG. 38 is a simplified diagram illustrating a magazine mounting orientation according to an embodiment of the present invention;

FIG. 39 is a variation of the magazine embodiment of the present invention in which cells are opened by an opener located at each cell;

FIGS. 41A to 41C are three views of sets of cells mounted under UAV wings according to a further embodiment of the present invention;

FIG. 43 is a variation of the floor embodiment of FIG. 42 in which cells are fixed in position.

DESCRIPTION OF SPECIFIC EMBODIMENTS OF THE INVENTION

Figure 1:
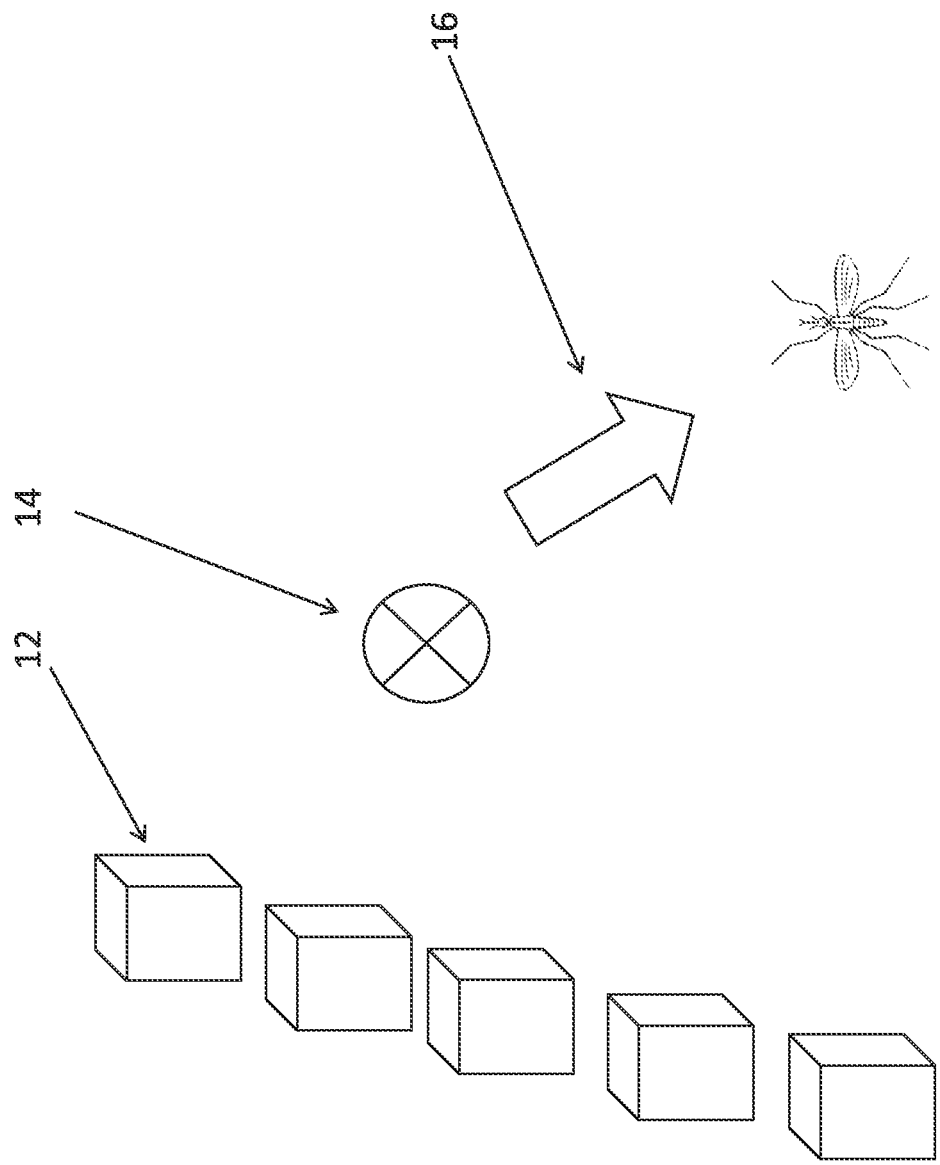
FIG. 1 is a simplified schematic diagram showing a mechanism for storage and release of insects from a drone or aerial vehicle according to embodiments of the present invention.

The present invention, in some embodiments thereof, relates to a device that can be carried by a drone which provides controlled and continuing release of insects and, more particularly, but not exclusively, to such a device for release of delicate insects such as mosquitoes.

The main challenges in general that exist today, are that a system is needed that can provide controlled release of insects over a sustained period of time so that a measured dose can be administered over a reasonable swath of territory to bring a wild insect population under control.

A controlled release of the insects makes for a best distribution of insects over a large area and maximizes insect distribution for the amount of energy used by the drone. Furthermore a controlled release allows for homogeneous coverage of an area.

Furthermore, as the density of the wild population is not constant, but rather is different per each location, and since the sterile mosquitoes cost money, it may be more cost effective to apply the required dosage and not more than that. Of course releasing less than the required dosage may end up in failing to achieve the suppression goals.

A drone is a light weight system and is limited by payload capacity.

Additional challenges include how to physically release the mosquitoes and provide a solution that is robust and allow most of the mosquitoes to be delivered from storage successfully to the wild.

The solution may include an ability to maintain cold temperature in order to knock down the mosquitoes so that the storage capacity is increased.

The solution may define how the storage-release unit is connected to the uav/drone.

If the drone has a propeller or rotary wing then the ideal solution may protect the mosquitoes from the effects of the propeller air flow.

The present embodiments may provide a modular storage-release system. Being modular, one can release a single storage-release unit each time above a designated release point. Being able to release one storage-release unit after the other say at designated intervals, provides the controllable and continuous release capability.

Being able to change the gaps or to release more than one module at once, may enable release of more mosquitoes at once—providing the capability to control the dosage.

The controlled dosage resolution may be in accordance with a smallest possible release unit capability by the system.

The storage may be coupled together as unit with the release device.

Embodiments may include an array or magazine of self-opening containers, carried or carryable by drone, each container or cell being individually controllable, to open and release insects according to desired locations and timings. The self-opening or individually openable cells contain insects and can be opened one by one at a predetermined rate and location in order to achieve continual or quasi-continual or controlled distribution of the insects by the drone.

The following embodiments are discussed herein:
1. Conveyor
2. Revolver (canister)
3. Moving boxes
4. Modular hexagons
5. Double sided door
6. Pulling from the back
7. Independently Triggered Cartridges Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1 is a schematic diagram that illustrates a storage and release mechanism for aerial distribution and release of insects from an unmanned aerial vehicle 10. The insects are stored in a storage unit 12, which is in some embodiments a single unit but in other embodiments comprises two or more cartridges. The mechanism comprises a switch 14 which switches between two or more different sustainable insect delivery rates for release of the insects via the unmanned aerial vehicle, and outlet 16.

The storage units 12 may retain the insects at cold temperature prior to release, and thus some form of refrigeration may be provided. A small refrigeration unit may be provided in each cartridge, or a single larger refrigeration unit may provide cold air to the cartridges, which have suitable connectors. The advantage of cold storage is that it causes the insects to sleep and makes them easier to store. In some of the embodiments, warm air can be supplied to the insects prior to release to wake them up.

Figure 2:
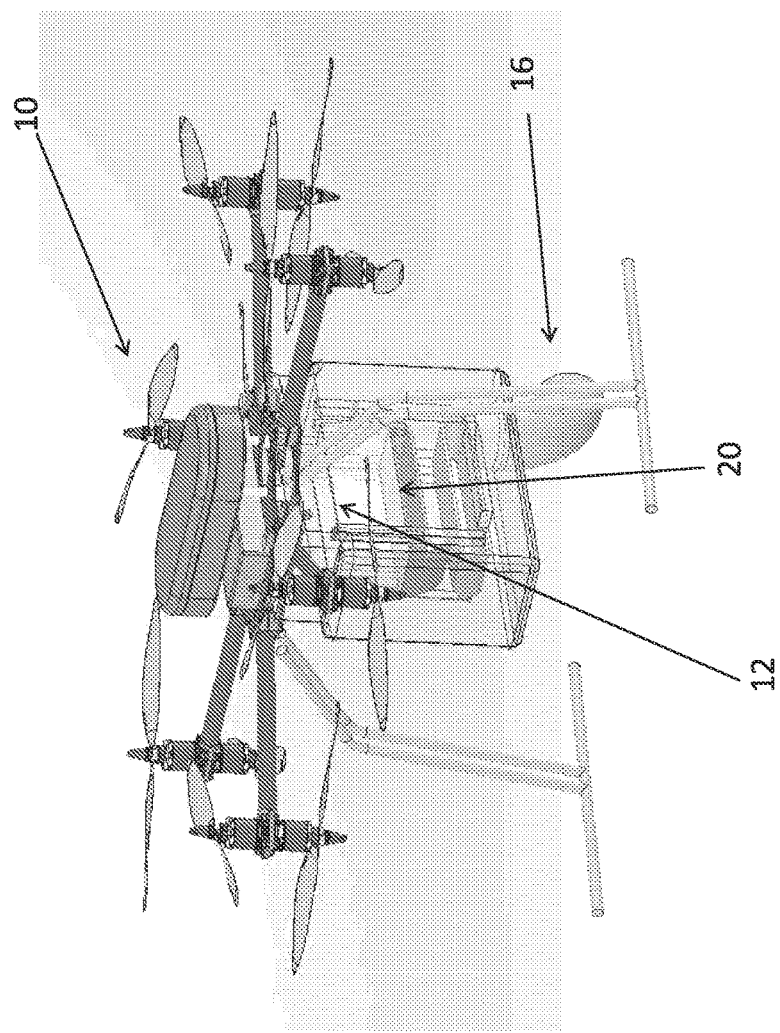
FIG. 2 is a simplified diagram showing an embodiment of the mechanism of FIG. 1.

Reference is now made to FIG. 2, which illustrates an embodiment of the storage and release mechanism of FIG. 1, in which the insects are released from storage 14 onto a conveyer 20. The switch 16 may set the speed of the conveyer and therefore define the delivery rate of the insects. The conveyor 20 may catch insects emptied from storage cartridges and deliver them to outlet 16. The storage and release mechanism is shown attached to the unmanned aerial vehicle 10.

Figure 3:
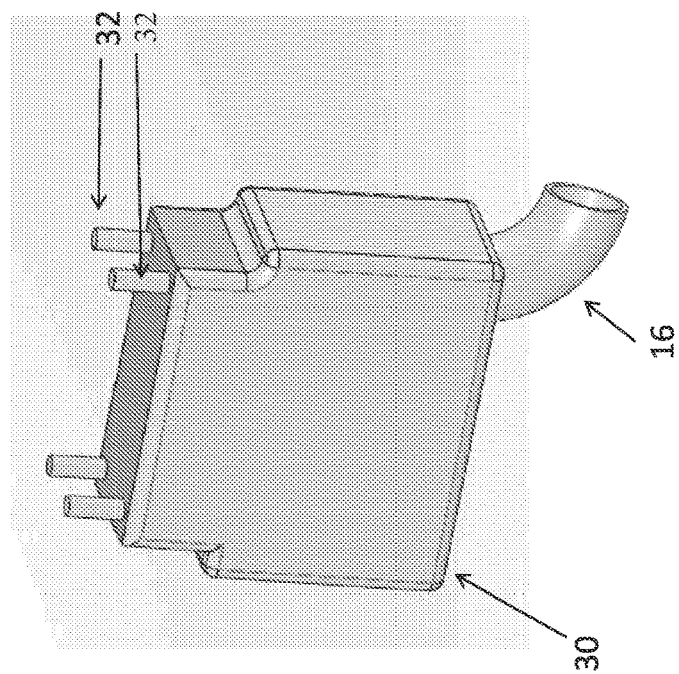
FIG. 3 is a detail of the embodiment shown in FIG. 2.

Reference is now made to FIG. 3, which is a view of storage and release mechanism 30 detached from the unmanned aerial vehicle 10. Quick release attachments 32 allow for easy attachment and release of the mechanism.

Reference is now made to FIG. 4, which is a cross-sectional view of the storage and release mechanism 30. A storage chamber 40 lies over conveyor 20 which forms the floor of the chamber. The chamber is kept cold. Insects fall off the edge of the conveyor 20 at exit point 42. Optional heating source 44 provides warm air for a heating area 46. A low power fan 48 blows air away from the exit point to ensure that warm air from the heating source 44 does not get into the storage area, and insects fall onto second conveyor 50, which transfers them to ejection cell 52 where they fall into outlet 16 and are expelled partly revived by the warm air. Expulsion may be gravitational, or an expulsion fan 54 may optionally be used. In particular, the outlet may be shaped as a chute to keep the exiting insects away from the rotors of the UAV and in this case, propulsion from the fan 54 may be needed.

A double conveyor structure is provided, and the speeds of the conveyors may regulate the rate at which mosquitoes are expelled from the device. The rate at which mosquitoes fall from storage onto the first conveyor can also be controlled, thus providing two ways that can work together to control the rate of expulsion. Using the two controls together provides a relatively fine control on the rate of expulsion of mosquitoes.

Reference is now made to FIG. 5A, which shows a design for a storage compartment 56 usable with the device of FIG. 4. There are no separate storage cartridges, and the conveyor 20 is in fact the floor of the storage unit. Conveyor 20 supplies insects to release cell 58. Isolation walls 60 ensure that insects remain inside unless fed by the conveyor 20. As shown in FIG. 5B, a trap door 62 can be used to keep insects in the release cell for a certain amount of time to allow them to revive. The door is useful if it is desired to ensure that insects are revived before release.

Figure 7:
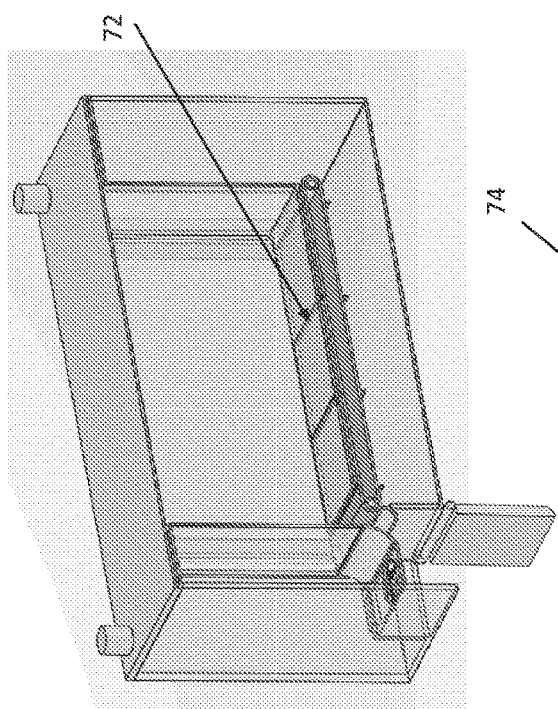
FIGS. 6-8 are three views of a variation of the embodiment of FIG. 2.
Figure 8:
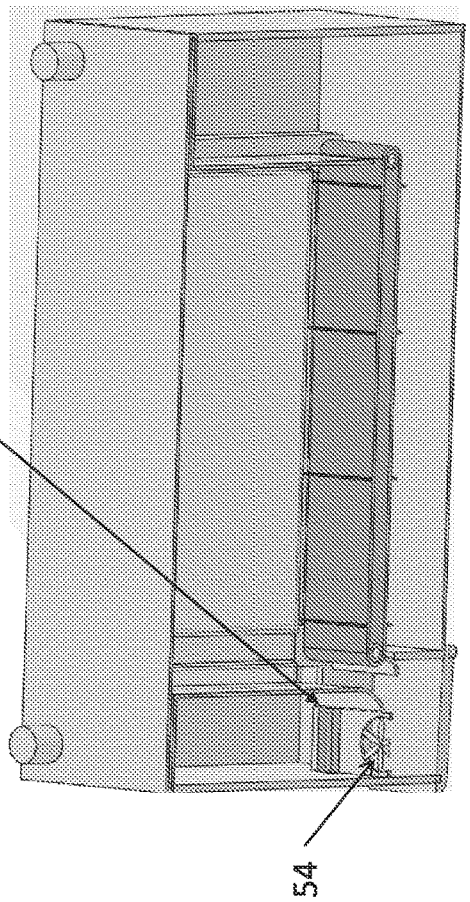
Figure 6:
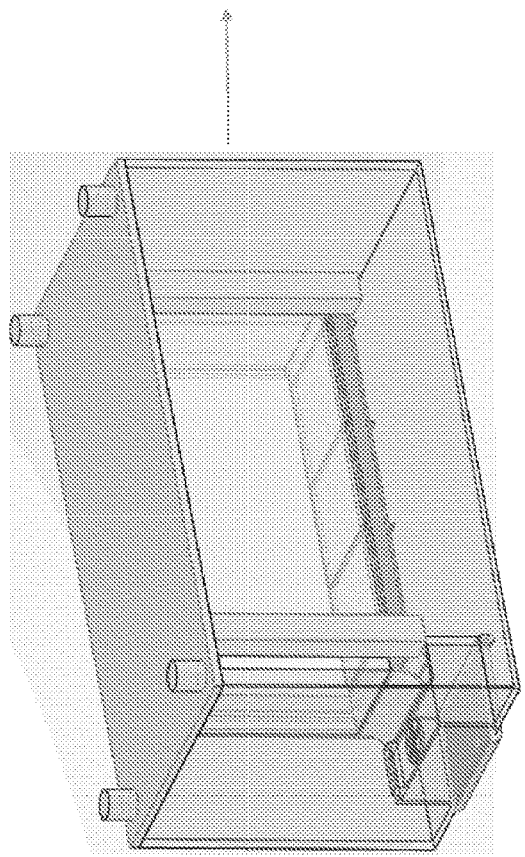
Figure 13:
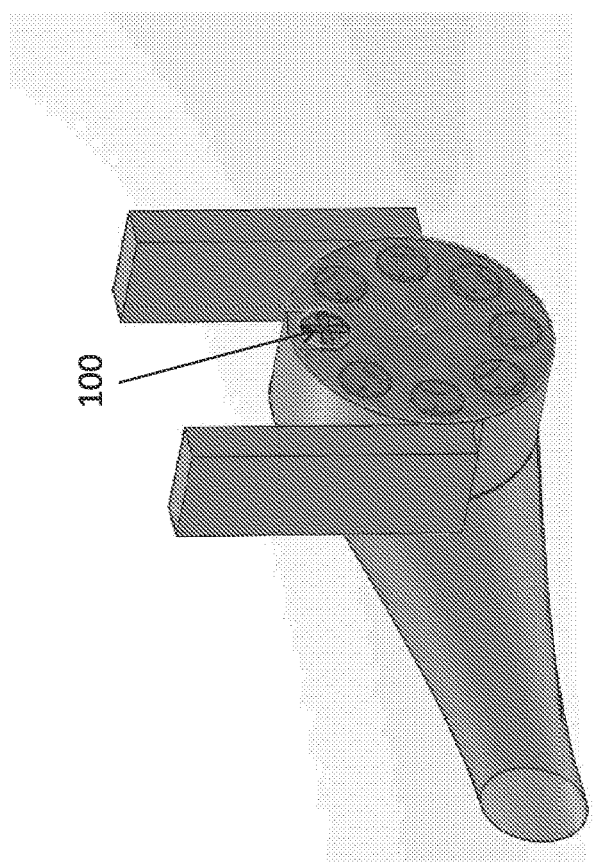
FIGS. 12, 13 and 14 illustrate fitting of a fan to the embodiment of FIG. 9.
Figure 14:
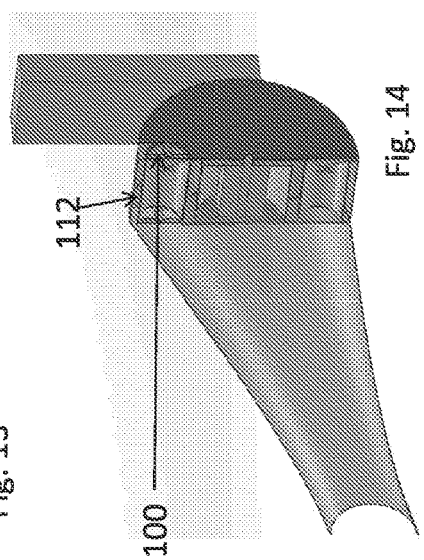
Figure 12:
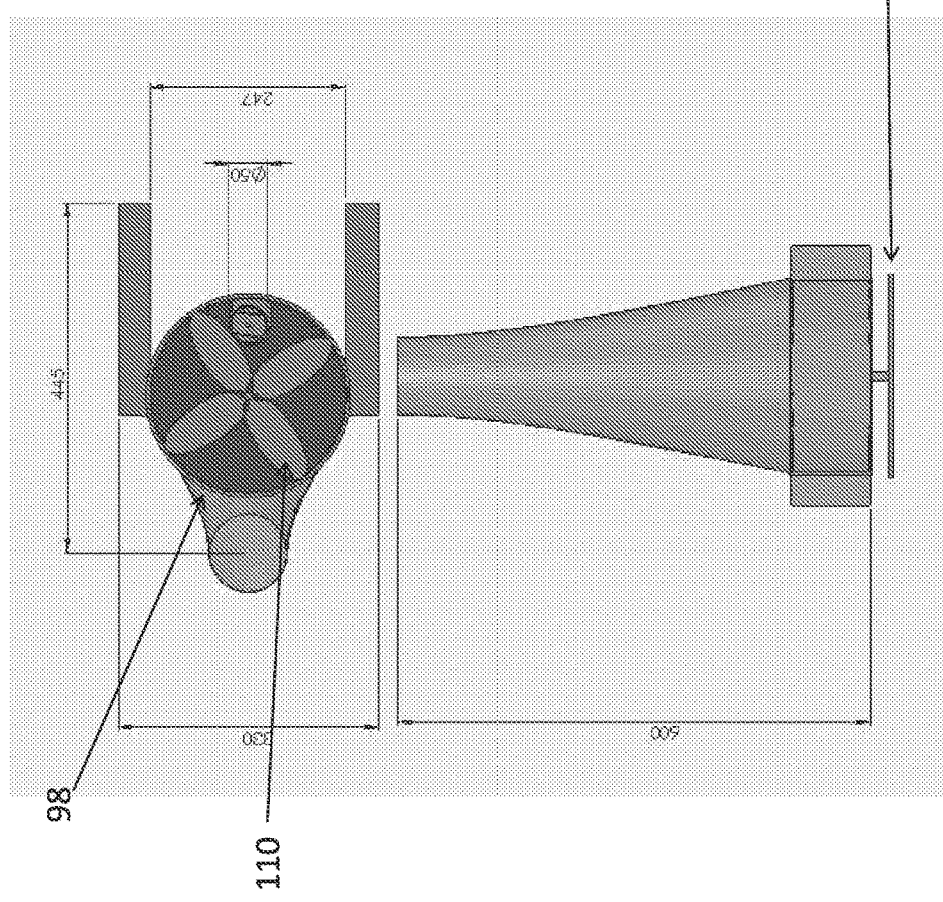
Figure 15:
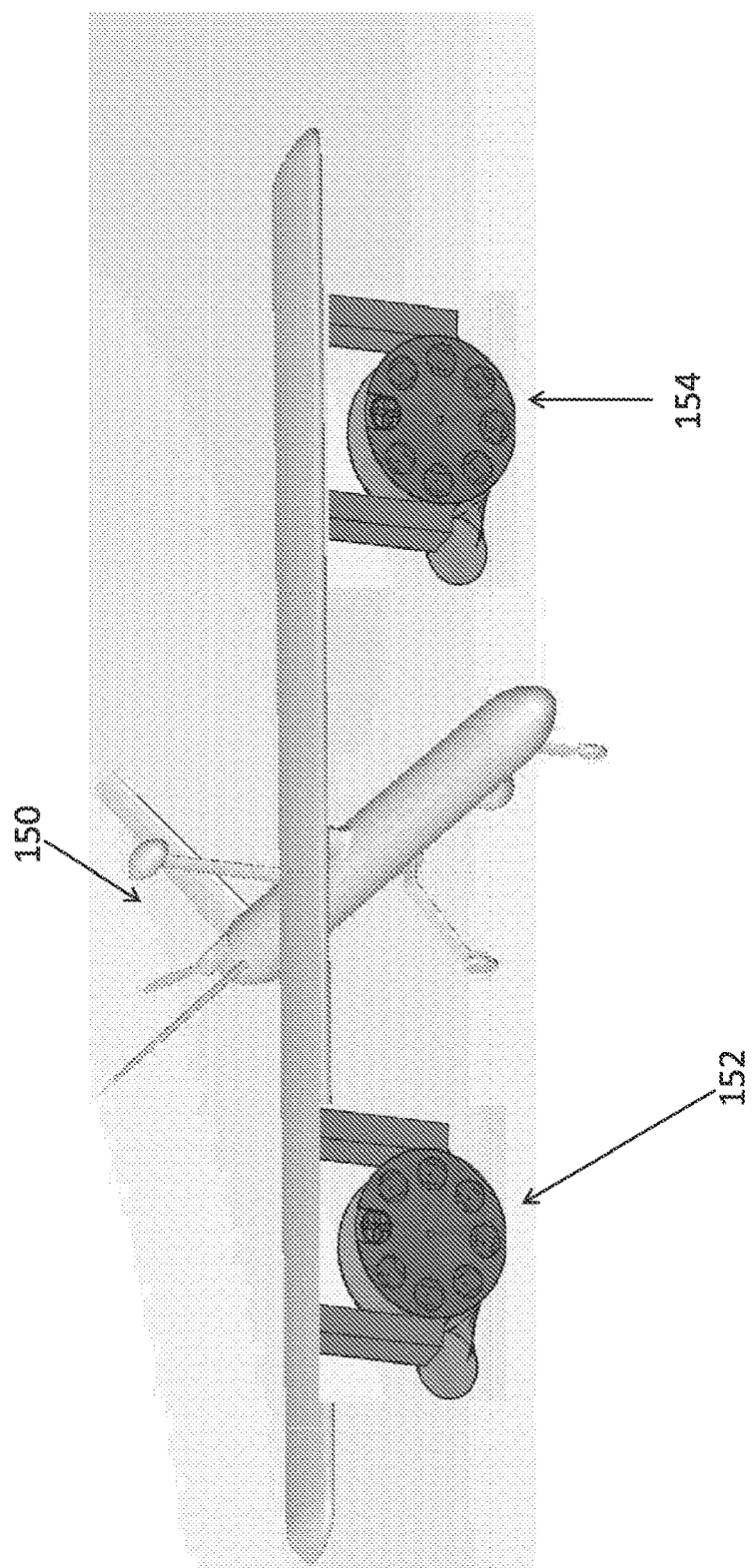
FIG. 15 illustrates the embodiment of FIG. 9 attached to a drone.

Reference is now made to FIGS. 6, 7 and 8, which are views of a variation 70 of the storage compartment and release chamber of FIG. 5. In the variation of FIGS. 7, 8 and 9, barriers 72 are provided on conveyor 20, that ensure that insects that have not yet reached the end of the conveyor do not exit to the release unit. Release unit 72 has heating source 74.

Once the release cell is filled then the conveyor may stop, the shutter or trap door 62 may open, either directly or after the last of the insects has a chance to revive, and the expulsion fan 54 may operate to expel the insects.

As soon as the release cell is empty then the fan 54 stops, the trap door/shutter 62 closes and the conveyor starts moving again at a calibrated rate.

For continuous release of revived insects, the double conveyor system of FIG. 4 is recommended. By adding the second conveyor 50 below conveyor 20, and then heating the second conveyor 50 the mosquitoes may fall onto the lower conveyor at a predefined rate, and the lower conveyor provides heating capability to slowly wake them up as they are transported to the release point. Preferably, heating is insufficient to awaken them fully so they don't start flying when still within the mechanism.

Reference is now made to FIG. 9, which is a simplified diagram showing an embodiment comprising radially arranged inserts for cartridges and a release mechanism. he idea is that a single release mechanism releases insects from the cartridges in turn as either the cartridges or the release mechanism revolve.

The storage unit 90 is structured as a revolver or revolving canister, with multiple inserts 92 for tubes, which can be regularly shaped tubes, to be installed and removed for reloading.

Figure 20:
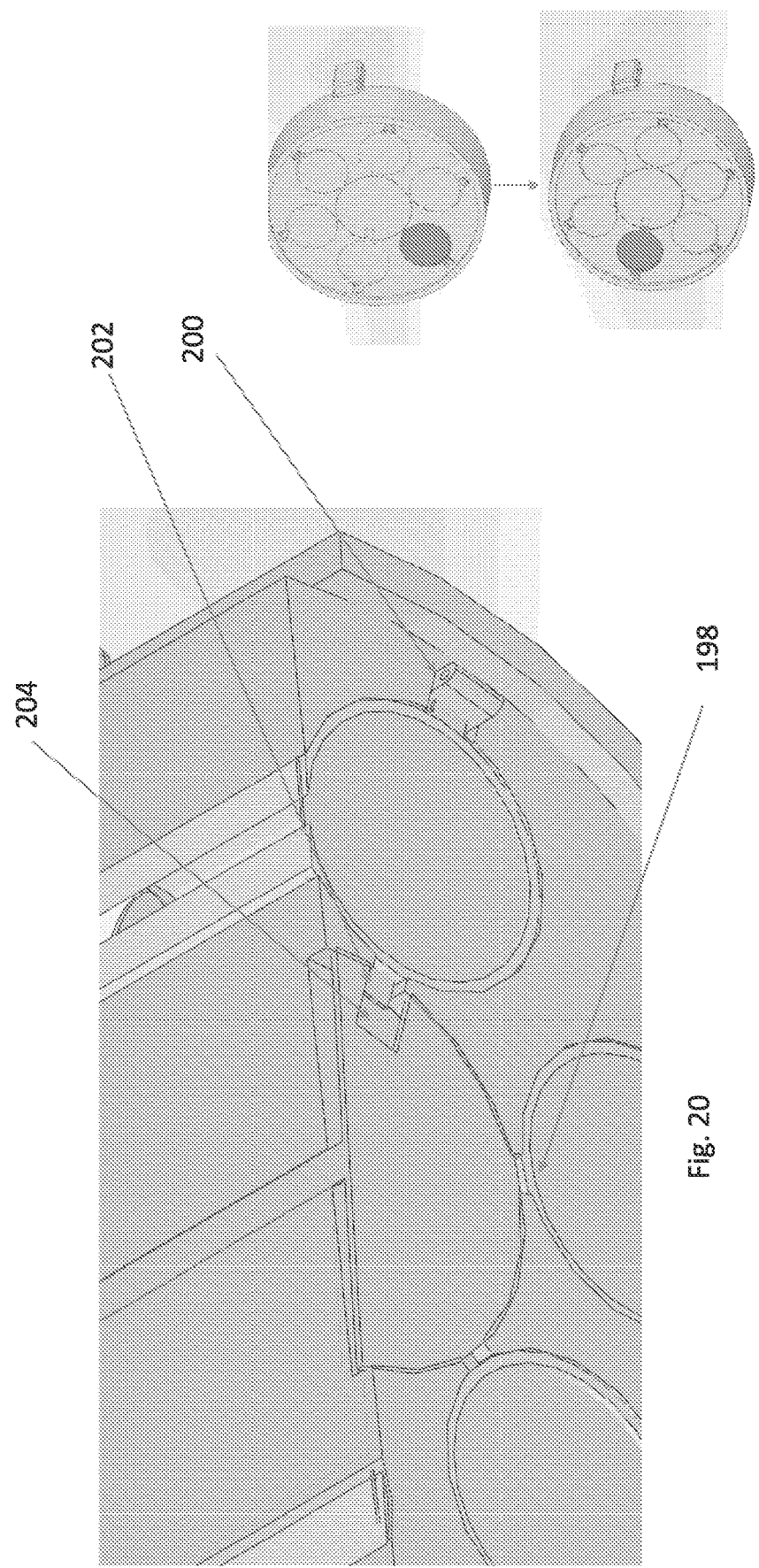
FIG. 20 is a detail showing latch operation in the embodiment of FIGS. 16-19.

In general, the storage unit operates by rotating the canister one place at a time. The cover plate revolves to the next tube, so that air coming from the outside or from a fan pushes out and releases the mosquitoes in the current tube.

Controlling the dosage may be achieved either by hovering while revolving the unit, increasing the release quantity above the same point, or increasing the revolving rate while flying—in all cases enabling the release of more mosquitoes per second.

It will be appreciated that the larger the drone, the larger the revolver may be.

The storage tubes may store insects both when knocked down and awake. The puff of air may release them to the outside.

The revolver comprises a revolving unit 90 which holds all the tubes in tube inserts 92. Tubes 94 are filled with mosquitoes and inserted into inserts 92 for use. After use they can be retrieved, refilled and reinserted.

A release chute 96 guides the mosquitoes from all of the release tubes, towards a single release opening 97. The release chute may be long enough to ensure that the insects are clear of the rotor or propeller and the effects thereof. The chute may be made of light materials such as carbon fibers and can be detached if needed.

A cover plate 98 fits over the back of the tubes and has a single air flow inlet 100 which may be opposite only one of the tubes at a given time. The tube opposite the air flow inlet is also opposite tube open outlet 101 through which the insects can be blown into the nozzle.

A mechanism may revolve either the cover plate or the tube holder around axis 102. The mechanism may include a motor.

As a variation, the external plate can have more than one opening so that more than one tube is emptied in parallel.

Thus the insects are arranged in a sequence of radially arranged cartridges, each cartridge sequentially being brought into contact with a release mechanism, either due to rotation of the cartridges or due to rotation of the release mechanism.

In the case of the cover plate rotating, a corresponding plate on the mosquito exit side, containing tube open outlet 101, also rotates in correspondence with plate 98.

Reference is now made to FIG. 10, which illustrates an embodiment in which the canister revolves and the release point 104 is fixed. Prior to reaching the release point 104 each tube spends time in a heating position 106 to revive the insects stored therein. The cover plate is not rotated by motor 108 and airflow through the release point 104 is constant.

Reference is now made to FIG. 11, which illustrates how a tube 94 can be removed and inserted into inserts 92. Two positions are shown, partially and fully inserted. The external cover 98 can be rotated to reveal a new insert. The tube may be made of isolated material, so without any active temperature control system, thus reducing system weight, it would take some time for the temperature to rise back to 8 degrees Celsius at which point the mosquitoes start to wake up and move, and thus require more space.

Reference is now made to FIG. 12, which shows how a fan 110 may be located in the air intake side of cover plate 98.

FIG. 13 shows air flow inlet hole 100 opposite one of the cartridge tubes. FIG. 14 is a cross sectional view showing a tube 112 opposite opening 100.

FIG. 15 illustrates a fixed wing drone 150 carrying two revolving canisters 152 and 154.

Reference is now made to FIG. 16, which is a simplified diagram illustrating a further embodiment of the present invention. Again tubes are arranged radially and each tube has a turn opposite an expulsion mechanism, either due to rotation of the expulsion mechanism or of the tube holder. In this case release is aimed downwards, the expulsion mechanism is a fan from above with an air inlet, and an insect outlet below, so that as the tube arrives in position, all of the insects are blown out of the tube by the fan. FIG. 16 is a view from below showing the canister 160, an open shutter 162 in the release position, all other shutters being closed, and fan 164 visible through the open tube. FIG. 17 is a view from above, showing the fan 164. FIG. 18 shows tubes 166 being inserted or released by opening the shutters 162, and then pushing the tubes into position and closing. A typical tube may have a diameter of 70 mm, and a length of 100 mm and have a capacity of some 40,000 mosquitoes. The canister may have a total capacity of 240,000 mosquitoes with six tubes.

Reference is now briefly made to FIG. 20, which is a simplified diagram showing the opening mechanism for the shutters. Each shutter 198 is spring loaded by spring 200 and held in placed by catch 202 which is held in a groove. At the release position, the groove opens out. The catch is no longer held and the shutter opens out. The effect may be enhanced by a slope 204 at the opening actively pushing the catch outwards.

Figure 21:
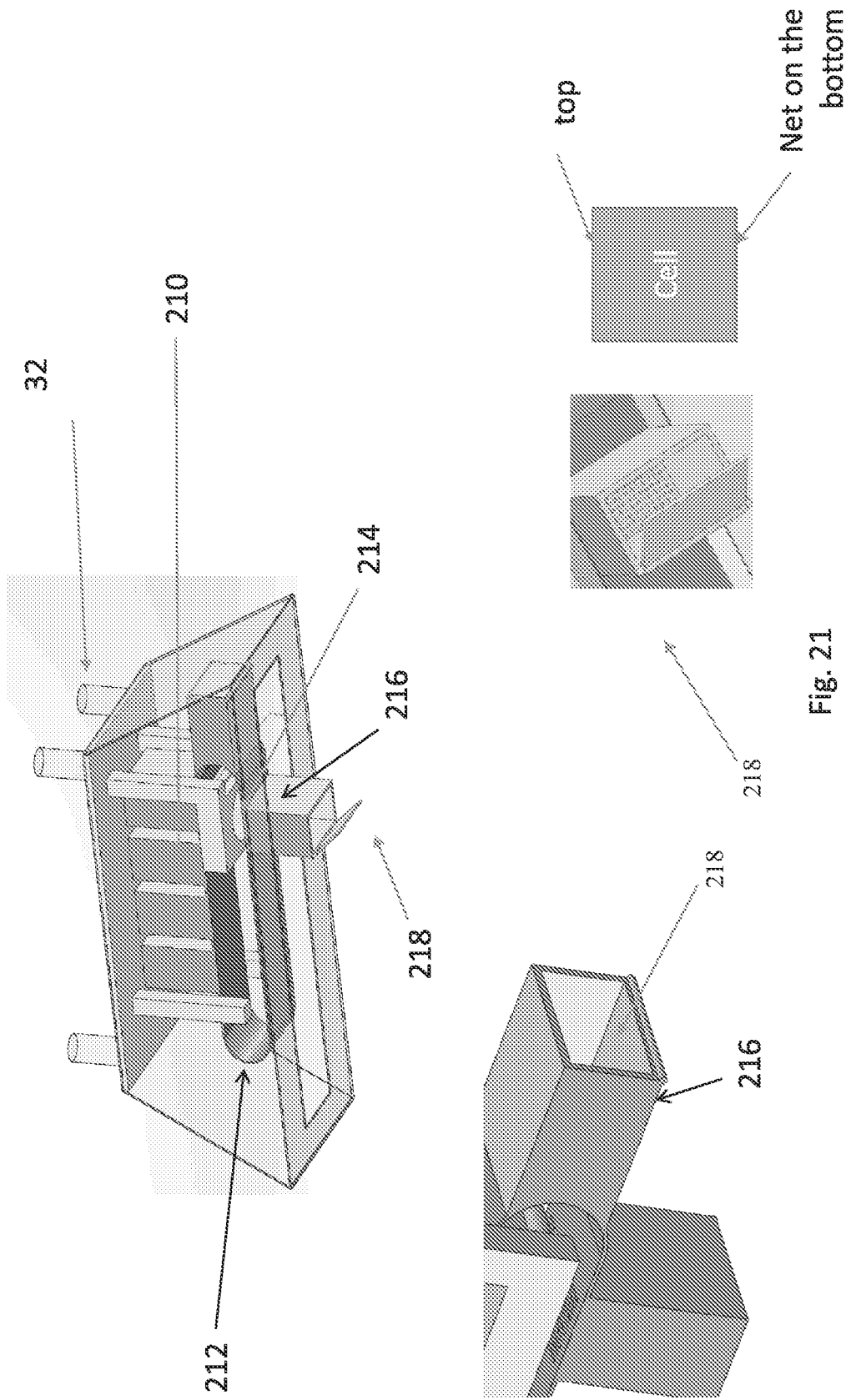

Reference is now made to FIG. 21 which illustrates a variation on revolving device in which cartridges, instead of revolving, travel linearly, say in a conveyor, to a point of expulsion.

As shown, a series of cartridges 210 are arranged on a conveyor 212 and move one by one to a release point 214 where a fan located above pushes the contents out through an exit mechanism 216 as the shutter 218 falls open upon inversion of the cartridge. The box may have netting at the lower opening to prevent exit anywhere therefrom except via the shutter when opened due to gravity. The cartridges may be heated prior to reaching the end of the conveyor, and the speed of the conveyor can be set as desired for the needed dose.

Figure 22:
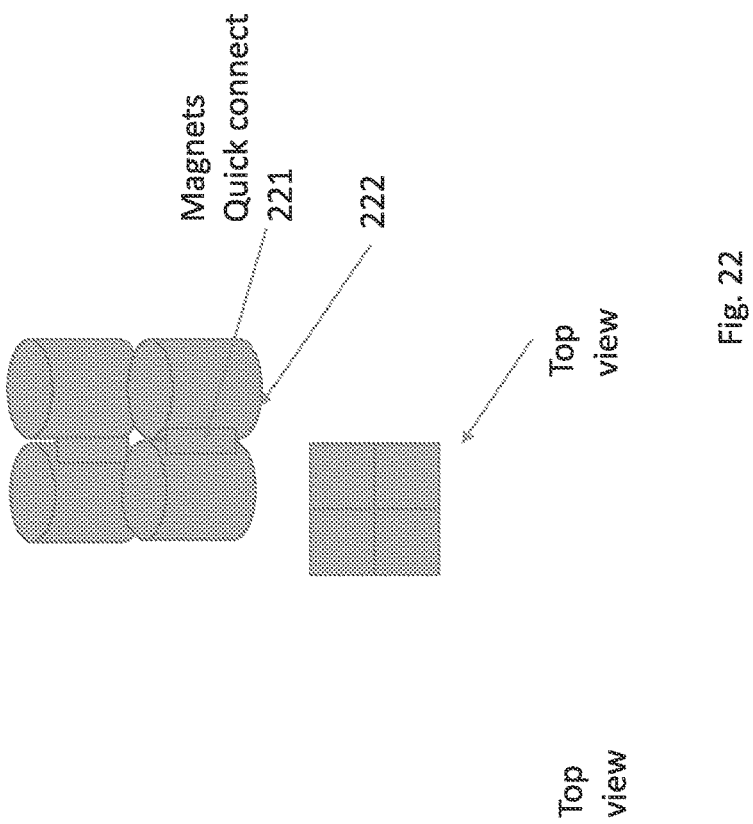

Reference is now made to FIG. 22, which shows top and perspective views respectively of modular cartridges 220, conveniently provided as hexagons, which are fitted together, say magnetically with magnets 221, and which have a shutter 222 which can be opened for the insects to fall out. The mechanism may thus provide a frame for attachment of a variable number of preloaded cartridges.

Each cartridge, for example provided as a tube, can be quickly disconnected, refilled and replaced. The size of the structure can be flexible—depending on the size of the UAV, say the Quadcopter, available number of mosquitoes etc. Thus less weight may equal more distance to fly and reach harder to get places, and therefore be more efficient to fly with smaller quantities.

The shutters may be actuated so that computerized control may open each container according to currently reached coordinates.

Figure 23:
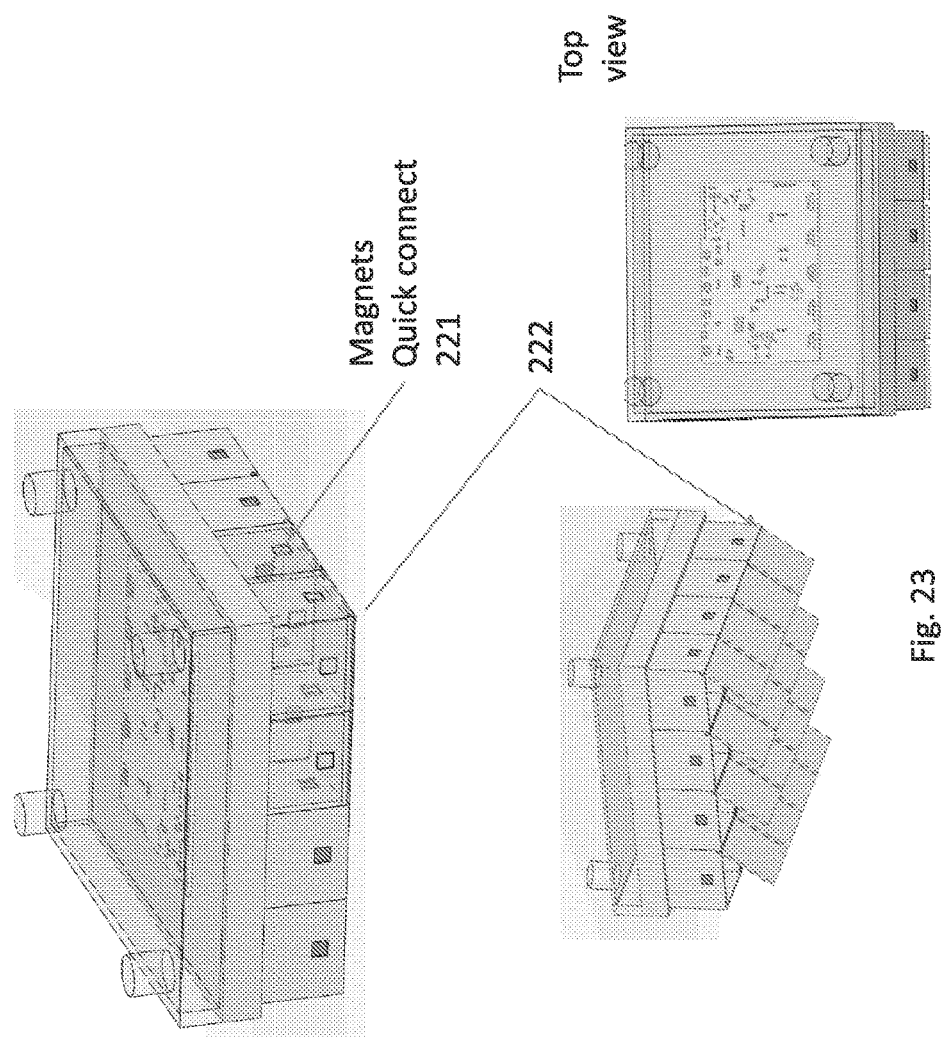

FIG. 23 shows the cartridges assembled into a canister and illustrates how the shutters 222 can open for each cartridge to be emptied.

FIG. 24 shows in greater details the quick connect magnets 221, and an optional cooling device 240 which may be provided for each unit.

The cells can either be opened independently at preset intervals, or multiple cells can be opened together as desired to control the dosage rate.

That is to say, storage is in many cartridges, and each cartridge has an independently actuatable opening.

The tube may have double doors, that is both at the inlet and outlet side. One door is to let insects out, and the other is to let air in, say from a fan to provide airflow to push out the insects. The fan may be controllable to different speeds in some of the embodiments.

Referring now to FIG. 25, a tube 250 has a door 252 at an air inlet end and a door 254 at an insect outlet end. The opening of the two doors may be synchronized so that the door 254 is opened before inlet door 252. FIG. 26 shows three such tubes attached to a wing of a fixed-wing drone. FIG. 27 shows the same view from behind at the inset outlet end and FIG. 28 shows the air inflow 280 and the insect outflow 282.

As well as locating the fan at the inlet end, it is also possible to reverse the fan to suck and to place the fan at the insect outlet end, taking care of course not to damage the insects.

Figure 29:
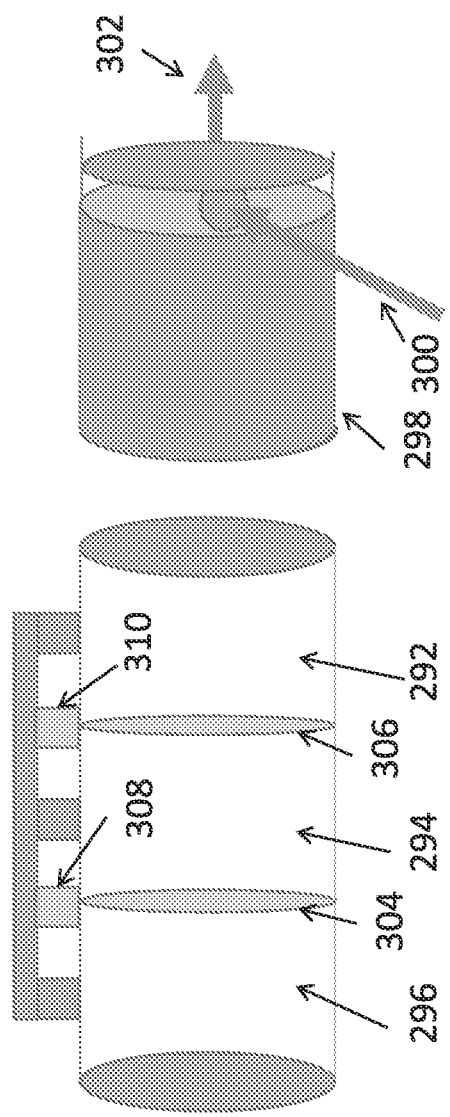

Reference is now made to FIG. 29 which shows a way of slowing down the rate at which a tube is emptied. Tube 290 is divided into separate lengths 292. 294 and 296, each of which is separately shuttered. The rearmost section 292 is emptied first, then the middle section 294 and then the front section 296. As the front of the tube is not available to the rearmost section at the start the tube requires suction and thus the fan is part of rear-mounted suction section 298. Airflow in line with arrows 300 and 302 causes suction, which pulls out the insects.

Divider doors 304 and 306 may be operated by door openers 308 and 310.

FIG. 30 shows emptying of the first stage 292. FIG. 31 shows start of emptying of the second stage 294. FIG. 32 shows middle stage 294 empty and FIG. 33 shows stage 296 open and ready to be emptied.

Figure 34:
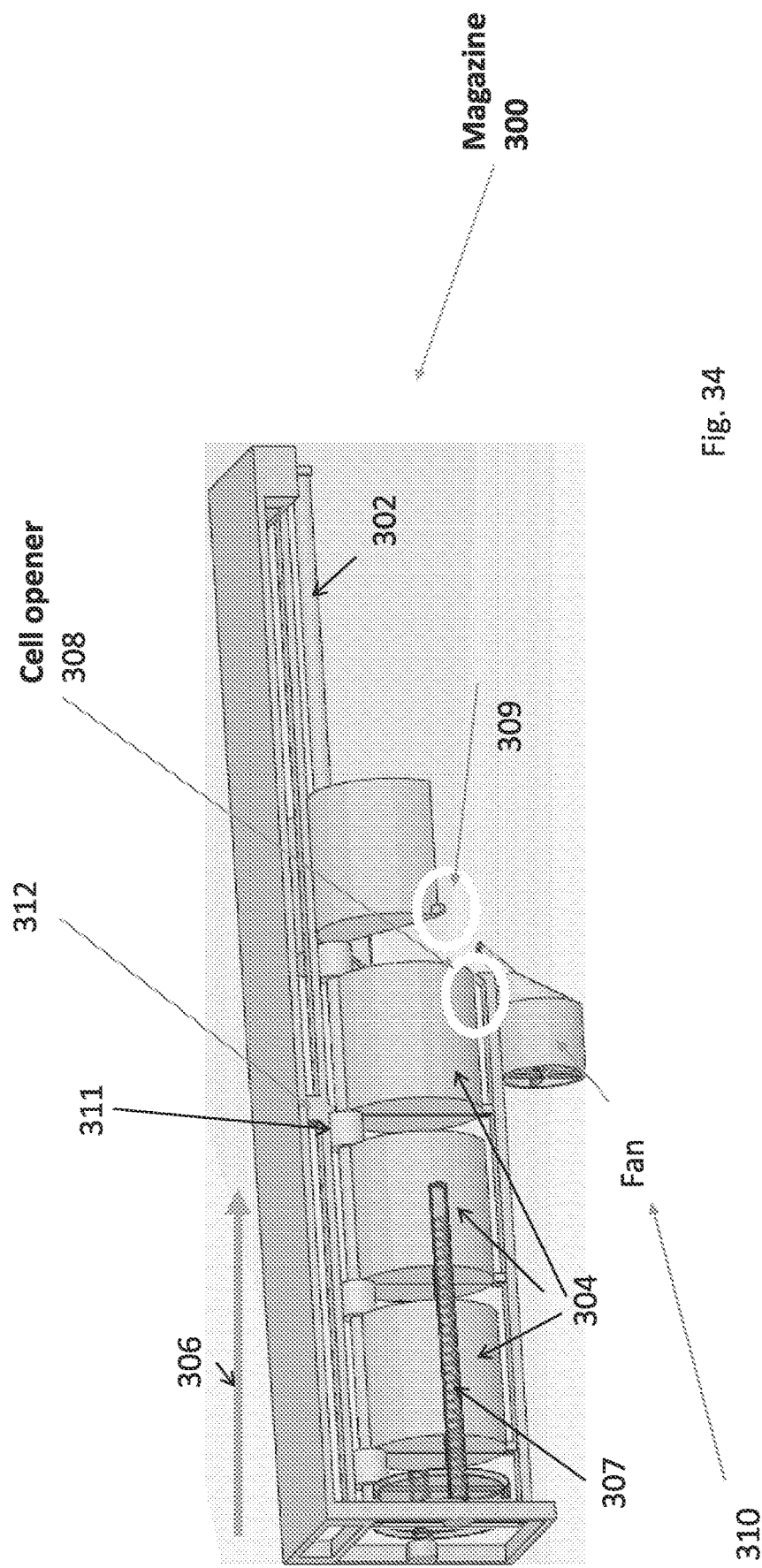
FIG. 34 is a simplified schematic diagram showing a magazine-based embodiment of the present invention.

FIG. 34 is a simplified schematic diagram showing a magazine-based embodiment of the present invention. Magazine 300 comprises rail 302 on which cells 304 ride in the direction of arrow 306. Spring 307 pushes the cells 304 along the rail in the direction of arrow 306 A cell opener 308 is located at an opening position and unlocks and opens the cells, say by depressing latch 309 on the cell, as they reach the opening position in their forward motion. Fan 310 is optional to help disperse the insects from the opened cells. Spacers 311 are optionally provided to maintain separation between successive cells. Stopper 312 stops the frontmost cell from proceeding to the opening position until a signal is given, as will be discussed in greater detail below. Typically the spacer 311 of the frontmost cell gets held by the stopper 312.

The stopper working together with the spacer provide a regulation mechanism for controlling the rate of insect release.

Figure 35:
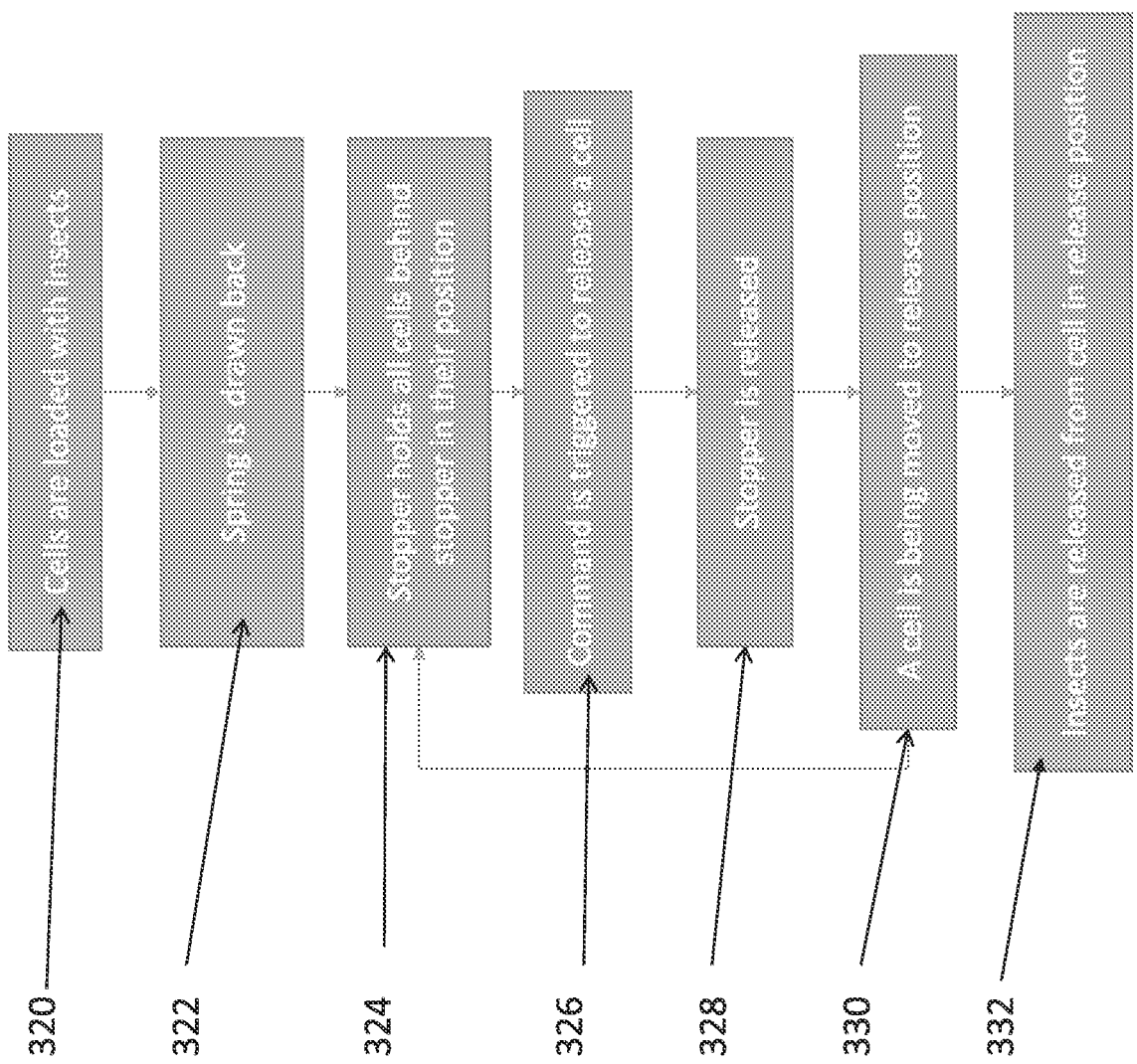
FIG. 35 is a simplified flow chart showing operation of the embodiment of FIG. 34.

FIG. 35 is a simplified flow chart showing operation of the embodiment of FIG. 34. Cells are loaded with insects—320. A spring is drawn back—322. A stopper holds individual cells in position—324. A release command is triggered 326. The corresponding stopper is released 328. A cell is moved to the release position, or opening position—330, and insects are released from the particular cell—332.

Figure 36:
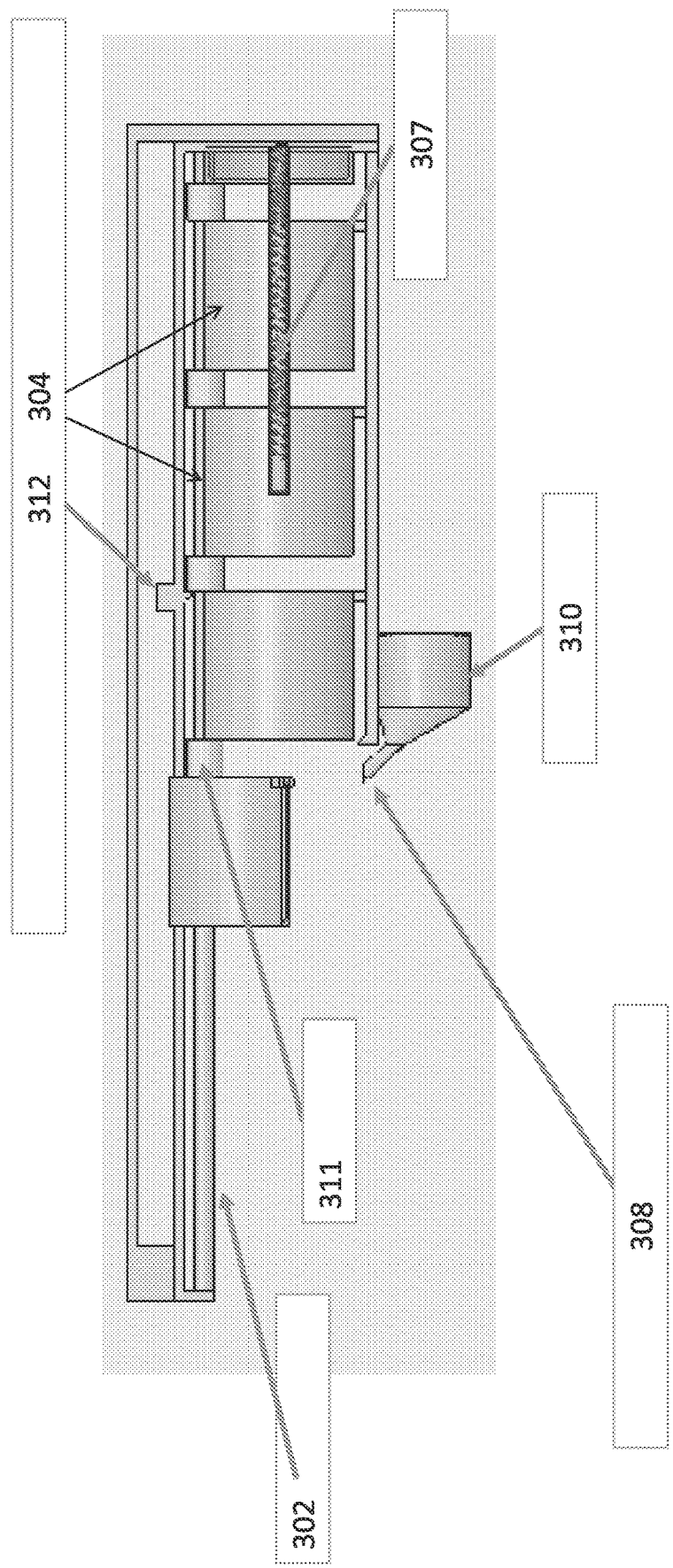
FIG. 36 is a simplified schematic diagram showing the embodiment of FIG. 34 in greater detail.

FIG. 36 is a simplified schematic diagram showing a detail of the embodiment of FIG. 34 in greater detail, in particular showing the mounting element 304, the stopper 312 and the opener 308. Magazine 300 comprises rail 302 on which cells 304 ride in the direction of arrow 306. Spring 307 pushes the cells 304 along the rail in the direction of arrow 306 A cell opener 308 is located at an opening position and unlocks and opens the cells, say by depressing latch 309 on the cell, as they reach the opening position in their forward motion. A fan 310 helps the insects to be distributed once they have been released from the current cell. Spacers 311 are optionally provided to maintain separation between successive cells. Stopper 312 stops the frontmost cell from proceeding to the opening position until a signal is given, as will be discussed in greater detail below. Typically the spacer 311 of the frontmost cell gets held by the stopper 312.

FIG. 37 is a simplified diagram showing one of the cells of FIG. 34, and showing the mechanical lock which is opened by the opener. Cell 304 has a mechanical latch 309. Opener 308 presses against the latch to open the cell. Spacer 311 abuts against stopper 312 and only advances to the opening position when stopper 312 is actuated to release the next cell in the direction of arrow 314.

The opener 308 may be folded away for opening.

FIG. 38 is a simplified diagram illustrating a magazine mounting orientation according to an embodiment of the present invention. The magazine mechanism of FIGS. 34 to 37 may be mounted on drone 350, either in parallel to the flying direction—352, or perpendicular to the flying direction—354.

FIG. 39 is a variation of the magazine embodiment of the present invention in which cells 360 are opened by an opener located at each cell. An opener may be provided for each cell individually. The opener is not shown in the drawing, but when actuated, presses on latch 362 to open the individual cell independently of the other cells. Reference numeral 364 indicates cells that have already been opened. Spacers 366 separate the cells which sit on rail 368.

An alternative provides a single opener (not shown in the drawing) that moves between the cells, for example along a screw thread, and opens a single cell each time.

Figure 40C:
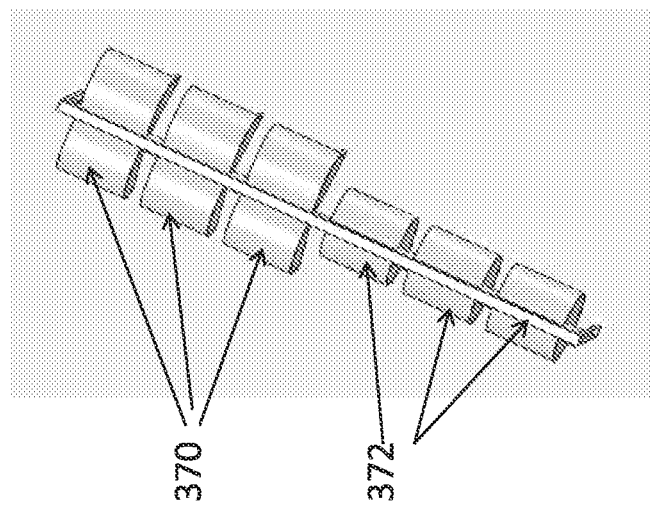
FIGS. 40A to 40D are four views of a set of cells of the magazine of FIG. 34.
Figure 40B:
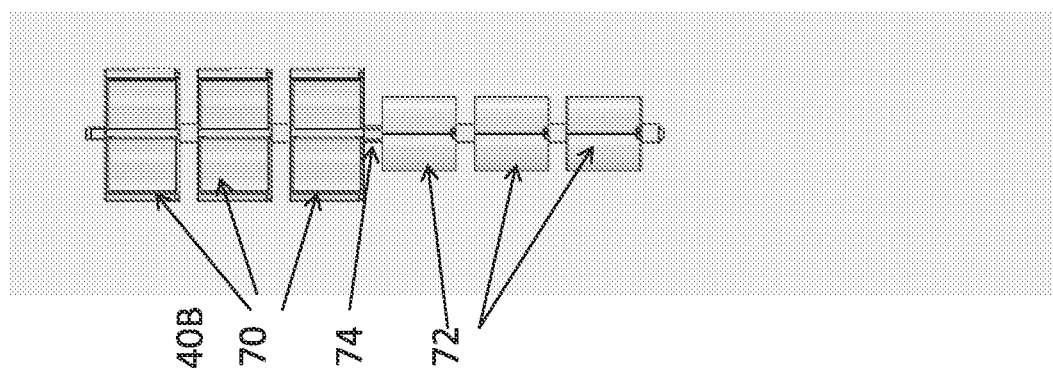
Figure 40A:
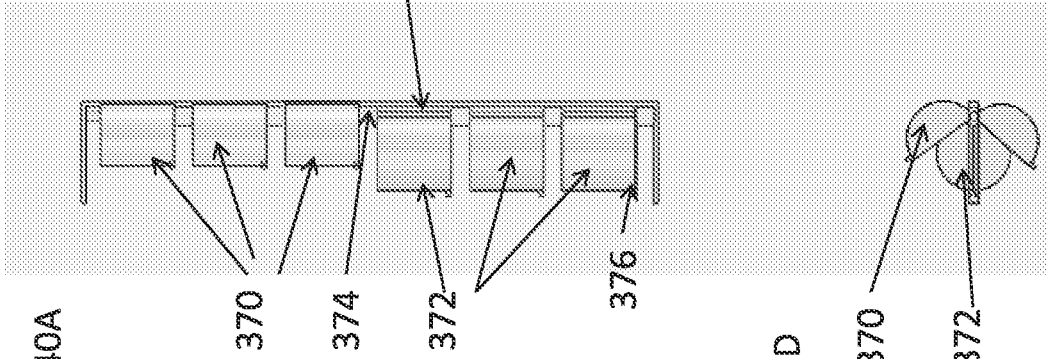

FIGS. 40A to 40D are four views of a set of cells of the magazine of FIG. 34. FIG. 40A is a side view.

FIG. 40B is a view from below of the same set of open and closed cells.

FIG. 40C is a view from above of the same set of open and closed cells. The views show open cells 370 and closed cells 372, separated by spacers 374. Latches 376 allow the cells to be opened, and rail 378 carries the cells.

Figure 40D:
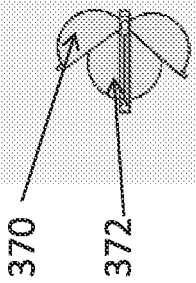

FIG. 40D is an end on view of a closed cell 372 seen behind an open cell 370.

FIGS. 41A to 41C are three views of sets of cells mounted under UAV wings according to a further embodiment of the present invention. Open cells 380 and closed cells 381 are lined up along wings 382 and 384 of UAV 386. FIG. 41A is a perspective view from above. FIG. 41B is a perspective view from below, and FIG. 41C is a perspective view from above when all of the cells are open.

Figure 42:
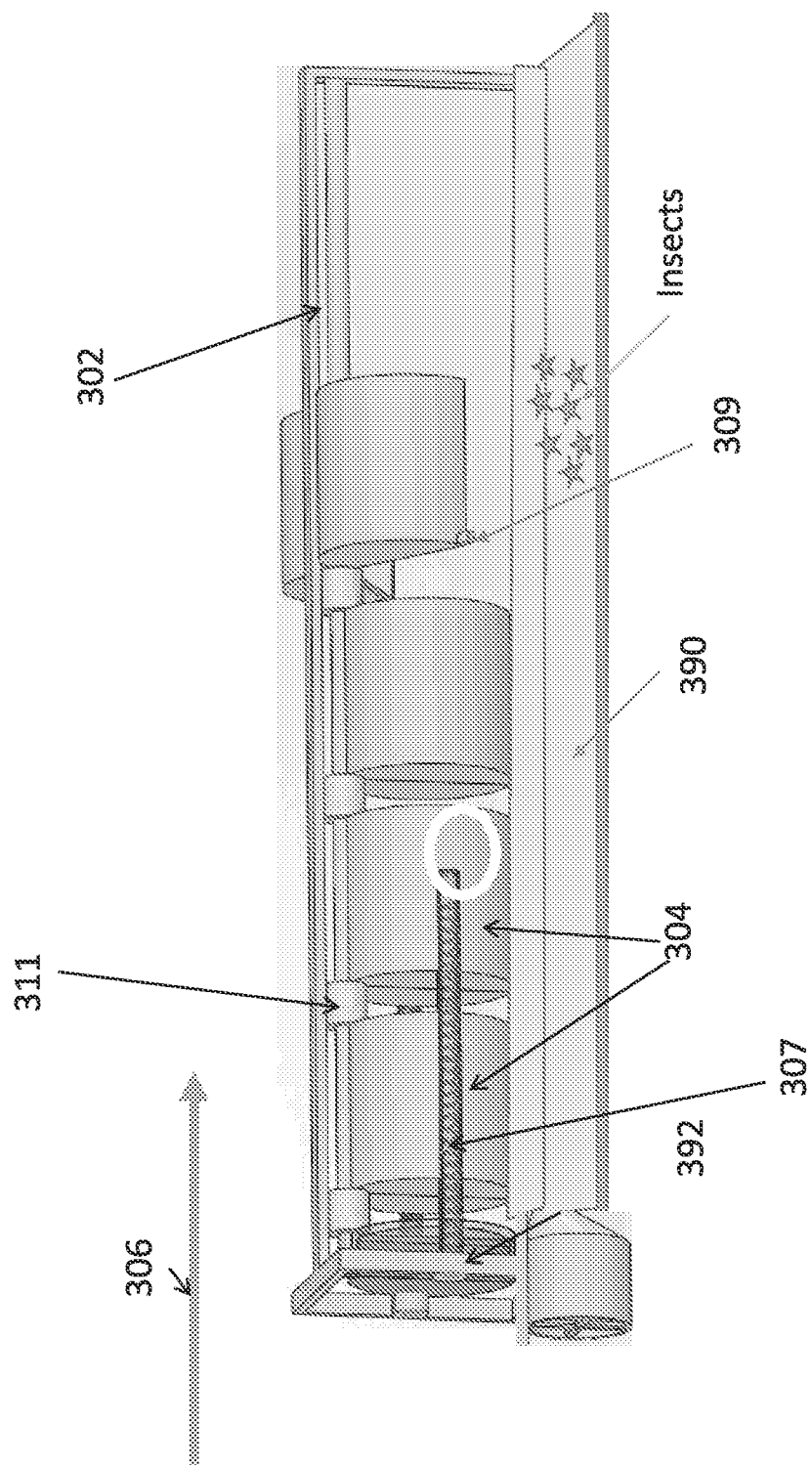
FIG. 42 is an embodiment in which cell release is onto a magazine floor, from which the insects are pushed out, according to an embodiment of the present invention.

FIG. 42 is a variation of the moving cell embodiment of FIG. 34 in which cell release is onto a magazine floor 390, from which the insects are pushed out by air blown from fan 392. For repeated features, reference numerals are the same as in FIG. 34 and are only referred to again where needed for an explanation of the present embodiment. Mosquitoes fall to the floor 390 as the cells are opened and are then dispersed by the fan 392 located at the far end. Adjusting the fan speed enables release of the cell content in a few bursts of air coming from the fan instead of a single release when the cell door is opened, so that the release rate may be modulated.

FIG. 43 is a variation of the floor embodiment of FIG. 42 in which cells are fixed in position as in the embodiment of FIG. 39. As with the embodiment of FIG. 39, an opener may be provided for each cell individually. The opener is not shown in the drawing, but when actuated, presses on latch 362 to open the individual cell independently of the other cells. Reference numeral 364 indicates cells that have already been opened. Spacers 366 separate the cells which sit on rail 368.

An alternative provides a single opener (not shown in the drawing) that moves between the cells, for example along a screw thread, and opens a single cell each time.

As the cells are opened, insects 400 are deposited on floor 402 and then distributed by blowing from fan 404.

It is expected that during the life of a patent maturing from this application many relevant unmanned aerial vehicle technologies will be developed and the scope of the corresponding terms are intended to include all such new technologies a priori.

The terms "comprises", "comprising", "includes", "including", "having" and their conjugates mean "including but not limited to".

The term "consisting of" means "including and limited to".

As used herein, the singular form "a", "an" and "the" include plural references unless the context clearly dictates otherwise.

It is appreciated that certain features of the invention, which are, for clarity, described in the context of separate embodiments, may also be provided in combination in a single embodiment, and the above description is to be construed as if this combination were explicitly written. Conversely, various features of the invention, which are, for brevity, described in the context of a single embodiment, may also be provided separately or in any suitable subcombination or as suitable in any other described embodiment of the invention, and the above description is to be construed as if these separate embodiments were explicitly written. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A storage and release mechanism for aerial distribution and release of insects from cartridges mounted on an unmanned aerial vehicle, the release being aimed at controlling a wild insect population, the wild population having fluctuating local densities, the mechanism comprising:
   the cartridges mounted on the unmanned aerial vehicle;
   a switch for switching between a first sustainable insect delivery rate for release of said insects via said unmanned aerial vehicle and a second sustainable insect delivery rate for release of said insects via said unmanned aerial vehicle to provide a selected insect delivery rate; and
   a release mechanism; wherein said insects are arranged in said mounted cartridges, each cartridge sequentially being brought into contact with said release mechanism at said selected delivery rate, the release mechanism configured to release said insects from each cartridge while the respective cartridge remains mounted on the unmanned aerial vehicle.

2. The storage and release mechanism of claim 1, wherein storage of said insects prior to release is in a cold storage, or wherein said insects are released from said storage onto a conveyor, said switch setting said conveyor in motion or setting a speed of said conveyor.

3. The storage and release mechanism of claim 1, both of said first and second sustainable insect delivery rates being finitely positive delivery rates.

4. The storage and release mechanism of claim 3, wherein the cartridges are radially arranged to rotate and the release mechanism is fixed.

5. The storage and release mechanism of claim 3, wherein the radially arranged cartridges are fixed and the release mechanism rotates around the cartridges.

6. The storage and release mechanism of claim 1, wherein said storage is in a plurality of cartridges, each cartridge being independently openable or having an independently actuatable opening.

7. The storage and release mechanism of claim 1, comprising a tube having an air inlet and an insect outlet end and a fan controllable to blow air through said tube to expel said insects.

8. The storage and release mechanism of claim 7, wherein said tube has a door at said air inlet end and a door at said insect outlet end, the openings of said doors being synchronized such that said door at said insect outlet end is opened before opening of said door at said air inlet end.

9. The storage and release mechanism of claim 7, wherein said fan is located at said air inlet end and pushes said insects out of said storage, or wherein said fan is located at said insect outlet end to pull said insects out of said storage.

10. The storage and release mechanism of claim 1, further comprising an expulsion mechanism to empty a recently opened cartridge.

11. The storage and release mechanism of claim 10, wherein the expulsion mechanism is movable towards a cartridge to be opened, or wherein the cartridge to be opened is moved towards said expulsion mechanism.

12. The storage and release mechanism of claim 1, said storage being in a plurality of cartridges, and wherein each cartridge is independently openable in a downward direction to allow gravity to cause the insects to fall out, or wherein said switch is configured to carry out said switching by defining a rate of opening of said cartridges, or wherein each cartridge has an independently actuatable opening, said cartridges being openable onto a collection floor, the mechanism further comprising an expulsion unit placed to disperse insects from said cartridges, said expulsion unit regulated to switch between said first sustainable release rate and said second sustainable release rate.

13. The storage and release mechanism of claim 12, wherein one of said sustainable insect delivery rates is set by opening at least two of said cartridges in parallel.

14. The storage and release mechanism of claim 1, comprising a plurality of insect-containing cartridges configured to proceed along a rail to an opening position, the opening position being associated with operation of a mechanical opener to open cells, the mechanism comprising an actuatable device to regulate arrival of cartridges at the opening position and thereby switch between said sustainable release rates.

15. The storage and release mechanism of claim 1, comprising a plurality of insect-containing cartridges openable onto a collection floor, and an expulsion unit placed to disperse insects released from said cartridges towards said collection floor, wherein regulation of said expulsion unit serves to switch between said sustainable release rates.

16. A storage and release mechanism for aerial distribution and release of insects from an unmanned aerial vehicle, the release being aimed at controlling a wild insect population, the mechanism comprising:

at least two cartridges containing insects for distribution, the cartridges configured for mounting on said unmanned aerial vehicle;

a controllable opening mechanism for controllably opening said cartridges to release said insects at a controllable rate, said controllable opening mechanism being configured to open said cartridges and release said insects from said cartridge while said cartridges remain mounted on said unmanned aerial vehicle; and a magazine, the magazine comprising an opening position and a mechanical opener, wherein said at least two insect-containing cartridges comprise a plurality of insect-containing cartridges within said magazine, the magazine configured to cause respective ones of said plurality of cartridges to proceed to said opening position, the opening position being a position at which each cartridge respectively is opened and the insects therein released, the opening position being associated with operation of said mechanical opener to open respective cartridges, the mechanism comprising an actuatable device being associated with said controllable opening mechanism to regulate arrival of cartridges at the opening position and thereby control said release rate.

17. The storage and release mechanism of claim 16, wherein said at least two cartridges are contained in said magazine and wherein said magazine is mounted lengthwise along a length of a wing of said unmanned aerial vehicle, or wherein said at least two cartridges are contained in said magazine and wherein said magazine is mounted perpendicular to a length of a wing of said unmanned aerial vehicle.

18. The storage and release mechanism of claim 16, wherein said magazine comprises a collection floor, wherein said at least two insect-containing cartridges comprise a plurality of insect-containing cartridges within said magazine, the plurality of insect-containing cartridges being openable onto said collection floor, or at least some of said cartridges having an independently actionable opening; and an expulsion unit placed to disperse insects released from said cartridges towards said collection floor, wherein regulation of said expulsion unit serves to control said release rate.

19. An unmanned aerial vehicle having at least two cartridges mounted thereon, each cartridge containing insects for release, each cartridge being controllably openable to release said insects from respective cartridges while said cartridges remain mounted on the unmanned aerial vehicle; the unmanned aerial vehicle further comprising a magazine, wherein said at least two insect-containing cartridges comprise a plurality of insect-containing cartridges within said magazine and configured to proceed to an opening position, the opening position being a position at which each cartridge respectively is mechanically opened and the insects therein released, the opening position being associated with operation of a mechanical opener to open said cartridges, the mechanism comprising an actuatable device to regulate arrival of cartridges at the opening position and thereby control said release rate.

20. A storage and release mechanism for insect dispersal from an unmanned aerial vehicle, the mechanism comprising:

a plurality of cartridges;

a conveyor extending from a storage position to a release position, for conveying insects in said cartridges from said storage position to said release position;

an insect release door fixed at said release position and a mechanical opener, said door being openable in synchronization with said conveying of insects along said conveyor, to release said insects for dispersal from said cartridges as respective cartridges are opened by said mechanical opener, the cartridges being retained on said unmanned aerial vehicle.

\* \* \* \* \*

UNITED STATES PATENT AND TRADEMARK OFFICE
CERTIFICATE OF CORRECTION

PATENT NO. : 11,584,526 B2
APPLICATION NO. : 16/082546
DATED : February 21, 2023
INVENTOR(S) : Hanan Lepek et al.

Page 1 of 1

It is certified that error appears in the above-identified patent and that said Letters Patent is hereby corrected as shown below:

On the Title Page

Item (54) and in the Specification Column 1 Line 1, Change "AERAIL" to --AERIAL--

Signed and Sealed this
Thirty-first Day of October, 2023

Katherine Kelly Vidal
*Director of the United States Patent and Trademark Office*